United States Patent
Sakai et al.

(10) Patent No.: US 6,214,481 B1
(45) Date of Patent: Apr. 10, 2001

(54) ORGANIC ELECTROLUMINESCENT DEVICE

(75) Inventors: Toshio Sakai; Hisahiro Higashi; Hiroaki Nakamura; Hisayuki Kawamura; Chishio Hosokawa, all of Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 08/941,036

(22) Filed: Sep. 30, 1997

(30) Foreign Application Priority Data

Oct. 8, 1996 (JP) .................................................. 8-267021

(51) Int. Cl.$^7$ .................................................. H05B 33/14
(52) U.S. Cl. .......................... 428/690; 428/917; 313/504; 313/506
(58) Field of Search ..................................... 428/690, 917, 428/691; 313/504, 506; 257/40, 94, 103

(56) References Cited

U.S. PATENT DOCUMENTS

| 5,413,887 | 5/1995 | Ueda . | |
|---|---|---|---|
| 5,503,910 | 4/1996 | Matsuura et al. . | |
| 5,536,949 | * 7/1996 | Hosokawa et al. | 257/40 |
| 5,554,450 | * 9/1996 | Shi et al. | 428/690 |
| 5,601,903 | * 2/1997 | Fujii et al. | 428/212 |
| 5,652,067 | * 7/1997 | Ito et al. | 428/690 |

OTHER PUBLICATIONS

Database WPI, Derwent Publications, AN 97–095426, JP 8–333283, Dec. 17, 1996.
Patent Abstracts of Japan, vol. 17, No. 632 (C–1132), Nov. 24, 1993, JP 05–194943, Aug. 3, 1993.

\* cited by examiner

*Primary Examiner*—Marie Yamnitzky
(74) *Attorney, Agent, or Firm*—Oblon, Spivak, McClelland, Maier & Neustadt, P.C.

(57) ABSTRACT

A practical, organic, blue-emitting EL device having a long life and having high luminous efficiency and good thermal stability. The device comprises organic compound layers, of which at least one is an organic blue-emitting layer, as sandwiched between a pair of electrodes, and is characterized in that the organic blue-emitting layer comprises an organic host compound having a fluorescence quantum efficiency of not smaller than 0.3 in a solid state and a fluorescent substance, and the organic host compound and the fluorescent substance are selected such that the device retains a monomeric blue-emitting ability, and that all the organic compound layers have a glass transition temperature of not lower than 75° C., while the organic compound layers adjacent to the organic blue-emitting layer have a glass transition temperature of not lower than 105° C.

3 Claims, No Drawings

ORGANIC ELECTROLUMINESCENT DEVICE

FIELD OF THE INVENTION

The present invention relates to an organic electroluminescent (EL) device, and more precisely, to a blue-emitting, organic EL device having a long life and having high luminous efficiency and good thermal stability.

BACKGROUND OF THE INVENTION

As being self-luminescent, EL devices have high visibility. In addition, they have high impact resistance as being completely solid devices. Therefore, the use of EL devices in various displays as light emitters is being widely noticed.

EL devices are grouped into inorganic EL devices in which are used inorganic compounds as light-emitting materials, and organic EL devices in which are used light-emitting organic compounds. Of those, organic EL devices have been being much studied and expected as light emitters in the coming generations, since they require a greatly reduced level of voltage, they can be easily small-sized, they consume small electric power, they can emit light in a mode of plane emission, and they can easily emit three primary colors.

Known are various structures of organic EL devices having a basic constitution of positive electrode/organic light-emitting layer/negative electrode and optionally provided with a hole injection and transportation layer and an electron injection layer, such as positive electrode/hole transportation layer/organic light-emitting layer/negative electrode, and positive electrode/hole transportation layer/organic light-emitting layer/electron injection layer/negative electrode, etc.

For such organic EL devices, for example, metal complexes of phenolato-substituted 8-hydroxyquinolines have been disclosed as blue-emitting materials (see Japanese Patent Application Laid-Open No. 5-198378). However, these are problematic in that their luminous efficiency is low to be at most 0.2 lumen(lm)/W or so. The reason is because the fluorescence quantum efficiency of the host compounds is low to be at most 0.07 or so. Doping of fluorescent substances into the host compounds is effective in prolonging the life of the doped host compounds, but is not in improving their luminous efficiency.

As luminous materials (host materials) for organic EL devices capable of emitting blue at high efficiency, distyrylarylene compounds have been disclosed (see Japanese Patent Application Laid-Open No. 2-247278). In addition, it has been disclosed that the doping of organic host compounds with fluorescent substances produces the improvement in the luminous efficiency of the doped organic host compounds while prolonging their life (see International Patent Application Laid-Open No. 94/06157).

Many of those blue-emitting compounds generally have a low glass transition temperature (Tg), since π-electrons are distributed in narrow regions therein and since they have a low molecular weight. Therefore, organic EL devices comprising those compounds are problematic in that their thermal stability is poor. Organic EL devices for outdoor applications or applications in vehicles require high-temperature storage stability generally at 75° C. or so. However, conventional organic EL devices are problematic in those applications in that, when they are kept at high temperatures of 75° C. or so, the color to be emitted by them varies and their luminous efficiency is lowered. For these reasons, the applications of organic EL devices are inevitably limited.

Given that situation, various studies have been made in order to improve the thermal stability of organic EL devices. One example is to modify luminous materials to have dimer or oligomer structures, thereby making the materials have an elevated glass transition temperature. For this, referred to is Japanese Patent Application Laid-Open No. 8-12600, which discloses compounds (phenylanthracene derivatives) having a glass transition temperature of 181° C. In this publication, they tried to improve the efficiency of their devices and to prolong the life thereof by mixing the hole transportation layer and the light-emitting layer. However, the devices disclosed have a luminous efficiency of at most 0.6 lm/W, which is lower than 1 lm/W, and the capacity of the devices is not satisfactory.

As has been mentioned hereinabove, no blue-emitting, organic EL devices having a long life, high efficiency and good thermal stability, which are all indispensable in their practical use, are unknown.

SUMMARY OF THE INVENTION

Given this situation, the object of the invention is to provide a practical, blue-emitting, organic EL device having a long life and having high luminous efficiency and good thermal stability.

We, the present inventors have assiduously studied in order to obtain an organic EL device having those favorable properties, and, as a result, have found that an organic EL device, in which the organic blue-emitting layer comprises an organic host compound having a specific fluorescence quantum efficiency and a fluorescent substance, and the organic host compound and the fluorescent substance are selected such that the device retains a monomeric blue-emitting ability, and in which the organic compound layers constituting the device have a specific glass transition temperature, meets the requirements. The invention has been attained on the basis of these findings.

Specifically, the invention provides an organic EL device comprising organic compound layers, of which at least one is an organic blue-emitting layer, as sandwiched between a pair of electrodes, which is characterized in that (1) the organic blue-emitting layer comprises an organic host compound having a fluorescence quantum efficiency of not smaller than 0.3 in a solid state, and a fluorescent substance, and the organic host compound and the fluorescent substance are selected such that the device retains a monomeric blue-emitting ability, and (2) all the organic compound layers have a glass transition temperature of not lower than 75° C., while the organic compound layers adjacent to the organic blue-emitting layer have a glass transition temperature of not lower than 105° C.

DESCRIPTION OF PREFERRED EMBODIMENTS OF THE INVENTION

The organic EL device of the invention has an organic blue-emitting layer comprising an organic host compound and a fluorescent substance.

The organic host compound which is one component constituting the organic blue-emitting layer is not specifically defined, provided that its function is such that holes and electrons are injected thereinto and are transported therethrough to be recombined together to give off fluorescence, that its fluorescence quantum efficiency is not smaller than 0.3, and that it forms, along with the fluorescent substance, the organic blue-emitting layer having a glass transition temperature of not lower than 75° C. Therefore, various compounds are employable herein.

For example, the organic host compound may be selected from distyrylarylene derivatives of a general formula (I):

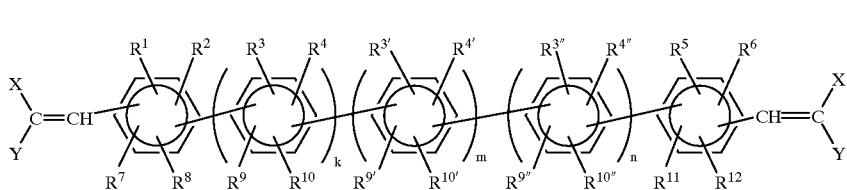

In formula (I), k, m and n each are 0 or 1, and (k+m+n) $\geq 1$. In the formula, $R^1$ to $R^{12}$ each independently represent a hydrogen atom, an alkyl group having from 1 to 6 carbon atoms, an alkoxy group having from 1 to 6 carbon atoms, an aryloxy group having from 6 to 18 carbon atoms, an aryl group having from 6 to 20 carbon atoms, an amino group, an alkylamino group, an arylamino group, a cyano group, a nitro group, a hydroxyl group, a halogen atom, or a group of:

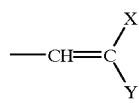

The alkyl group having from 1 to 6 carbon atoms includes, for example, a methyl group, an ethyl group, an n-propyl group, an i-propyl group, an n-butyl group, an i-butyl group, a sec-butyl group, a t-butyl group, an i-pentyl group, a t-pentyl group, a neopentyl group, an n-hexyl group, and an i-hexyl group. The alkoxy group having from 1 to 6 carbon atoms includes, for example, a methoxy group, an ethoxy group, an n-propoxy group, an i-propoxy group, an n-butyloxy group, an i-butyloxy group, a sec-butyloxy group, an i-pentyloxy group, a t-pentyloxy group, and an n-hexyloxy group. The aryloxy group having from 6 to 18 carbon atoms includes, for example, a phenoxy group, and a naphthyloxy group. The aryl group having from 6 to 20 carbon atoms includes, for example, a phenyl group, and a naphthyl group. The amino group is represented by -NH$_2$; the alkylamino group is by —NHR or —NR$_2$ (where R indicates an alkyl group having from 1 to 6 carbon atoms); and the arylamino group is by —NHAr or —NAr$_2$ (where Ar indicates an aryl group having from 6 to 20 carbon atoms).

The halogen atom includes, for example, a fluorine atom, a chlorine atom, a bromine atom, and an iodine atom.

Where k=1 and m=n=0 in formula (I), the substituents in at least one combination of $R^1$ and $R^2$, $R^3$ and $R^4$, $R^5$ and $R^6$, $R^7$ and $R^8$, $R^9$ and $R^{10}$, and $R^{11}$ and $R^{12}$ are bonded to each other to form a saturated or unsaturated, 5-membered or 6-membered ring. In that case, the substituents maybe bonded via a hetero atom (N, O, S) to form the ring. As specific examples where $R^1$ and $R^2$, $R^9$ and $R^{10}$, and $R^5$ and $R^6$ each are bonded to each other to form an unsaturated 6-membered ring, mentioned are compounds of the following formula:

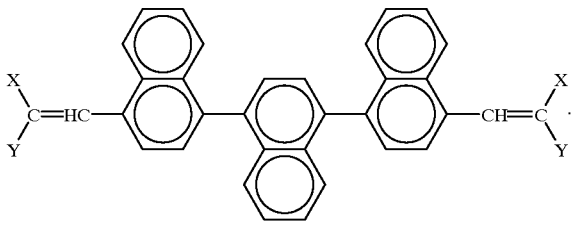

As specific examples where $R^7$ and $R^8$ are bonded to each other via a hetero atom O to form a saturated 5-membered ring, $R^{11}$ and $R^{12}$ are bonded to each other via a hetero atom N to form a saturated 5-membered ring, and $R^3$ and $R^4$, and $R^9$ and $R^{10}$ each are bonded to each other to form a saturated 6-membered ring, mentioned are compounds of the following formula:

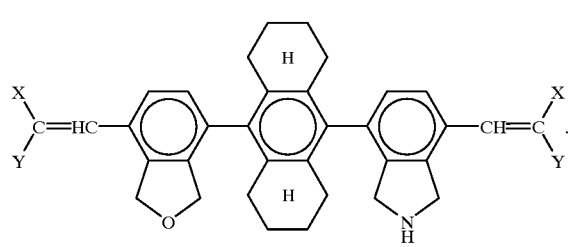

Where k=m=1 and n=0 in formula (I), the compounds are represented by the following formula:

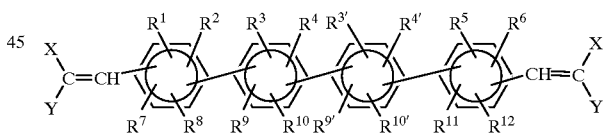

wherein $R^{3'}$, $R^{4'}$, $R^{9'}$ and $R^{10'}$ each independently represent a hydrogen atom, an alkyl group having from 1 to 6 carbon atoms, an alkoxy group having from 1 to 6 carbon atoms, an aryloxy group having from 6 to 18 carbon atoms, an aryl group having from 6 to 20 carbon atoms, an amino group, an alkylamino group, an arylamino group, a cyano group, a nitro group, a hydroxyl group, a halogen atom, or a group of:

and $R^1$ to $R^{12}$ have the same meanings as above.

In those, $R^1$ and $R^2$, $R^3$ and $R^4$, $R^{3'}$ and $R^{4'}$, $R^5$ and $R^6$, $R^7$ and $R^8$, $R^9$ and $R^{10}$, $R^{9'}$ and $R^{10'}$, and $R^{11}$ and $R^{12}$ each may be or may not be bonded to each other to form a saturated or unsaturated, 5-membered or 6-membered ring. Optionally, they may be bonded to each other via a hetero atom (N, O, S) to form the ring.

$R^2$ and $R^3$, $R^4$ and $R^{3'}$, $R^{4'}$ and $R^5$, $R^8$ and $R^9$, $R^{10}$ and $R^{9'}$, and $R^{10'}$ and $R^{11}$ each may be or may not be bonded to each other to form a saturated or unsaturated, 5-membered or 6-membered ring. Optionally, they may be bonded to each other via a hetero atom (N, O, S) to form the ring.

As specific examples where $R^2$ and $R^3$, $R^{10}$ and $R^{9'}$, and $R^{4'}$ and $R^5$ each are bonded to each other to form a saturated 5-membered ring, mentioned are compounds of the following formula:

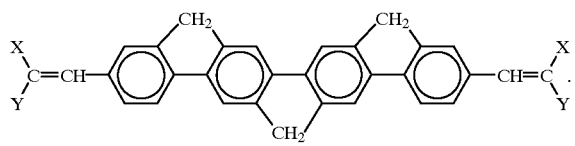

As those where $R^4$ and $R^{3'}$, and $R^{10}$ and $R^{9'}$ each are bonded to each other to form a saturated 6-membered ring, mentioned are compounds of the following formula:

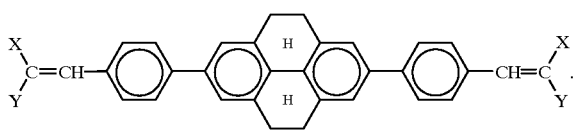

As those where $R^{10}$ is a group of:

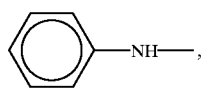

and $R^{9'}$ is a hydrogen atom to give a 5-membered ring, mentioned are compounds of the following formula:

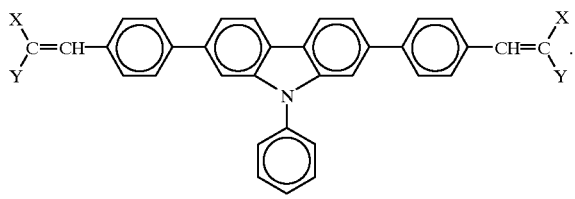

Where k=m=n=1 in formula (I), the compounds are represented by the following formula:

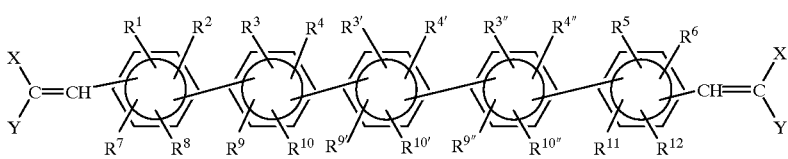

wherein $R^{3''}$, $R^{4''}$, $R^{9''}$ and $R^{10''}$ each independently represents a hydrogen atom, an alkyl group having from 1 to 6 carbon atoms, an alkoxy group having from 1 to 6 carbon atoms, an aryloxy group having from 6 to 18 carbon atoms, an aryl group having from 6 to 20 carbon atoms, an amino group, an alkylamino group, an arylamino group, a cyano group, a nitro group, a hydroxyl group, a halogen atom, or a group of:

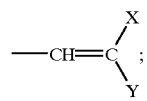

and $R^1$ to $R^{12}$, $R^{3'}$, $R^{4'}$, $R^{9'}$ and $R^{10'}$ have the same meanings as above.

In those, $R^1$ and $R^2$, $R^3$ and $R^4$, $R^{3'}$ and $R^{4'}$, $R^{3''}$ and $R^{4''}$, $R^5$ and $R^6$, $R^7$ and $R^8$, $R^9$ and $R^{10}$, $R^{9'}$ and $R^{10'}$, $R^{9''}$ and $R^{10''}$, and $R^{11}$ and $R^{12}$ each may be or may not be bonded to each other to form a saturated or unsaturated, 5-membered or 6-membered ring. Optionally, they may be bonded to each other via a hetero atom (N, O, S) to form the ring.

$R^2$ and $R^3$, $R^4$ and $R^{3''}$, $R^{4''}$ and $R^{3'}$, $R^{4'}$ and $R^5$, $R^8$ and $R^9$, $R^{10}$ and $R^{9'}$, $R^{10'}$ and $R^{9''}$, and $R^{10''}$ and $R^{11}$ each may be or may not be bonded to each other to form a saturated or unsaturated, 5-membered or 6-membered ring. Optionally, they may be bonded to each other via a hetero atom (N, O, S) to form the ring.

As specific examples where $R^8$, $R^9$, $R^{10''}$ and $R^{11}$ each are a group of:

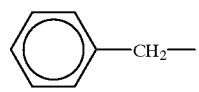

to form an unsaturated 5-membered ring, and $R^{3'}$ and $R^{4'}$ together form a saturated 5-membered ring via a hetero atom N, mentioned are compounds of the following formula:

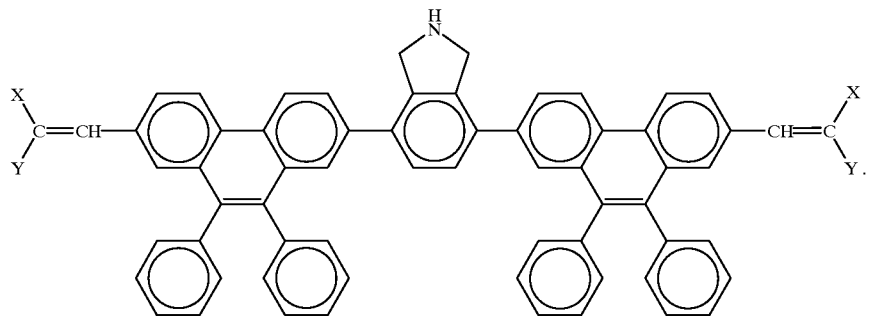

X and Y each independently represent an aryl group having from 6 to 20 carbon atoms, such as a substituted or unsubstituted phenyl, naphthyl, biphenyl, terphenyl, anthraryl, phenathryl, pyrenyl or perylenyl group.

The substituent includes, for example, an alkyl group having from 1 to 6 carbon atoms, such as a methyl group, an ethyl group, an n-propyl group, an i-propyl group, an n-butyl group, an i-butyl group, a sec-butyl group, a t-butyl group, an i-pentyl group, a t-pentyl group, a neopentyl group, an n-hexyl group, an i-hexyl group; an alkoxy group having from 1 to 6 carbon atoms, such as a methoxy group, an ethoxy group, an n-propoxy group, an i-propoxy group, an n-butyloxy group, an i-butyloxy group, a sec-butyloxy group, an i-pentyloxy group, a t-pentyloxy group, an n-hexyloxy group; an aryloxy group having from 6 to 18 carbon atoms, such as a phenoxy group, a naphthyloxy group; a phenyl group, an amino group, an alkylamino group, an arylamino group, a cyano group, a nitro group, a hydroxyl group; and a halogen atom, such as a fluorine atom, a chlorine atom, a bromine atom, an iodine atom. The group of X and Y may be substituted with one or more of those substituents.

X and Y and optionally their substituents may be bonded together to form a substituted or unsubstituted, saturated 5-membered, or saturated 6-membered ring. As specific examples of the styryl compounds where X and Y form a saturated, 5-membered or 6-membered ring, mentioned are the following compounds where X and Y form a saturated 5-membered ring, k=m=1 and n=0:

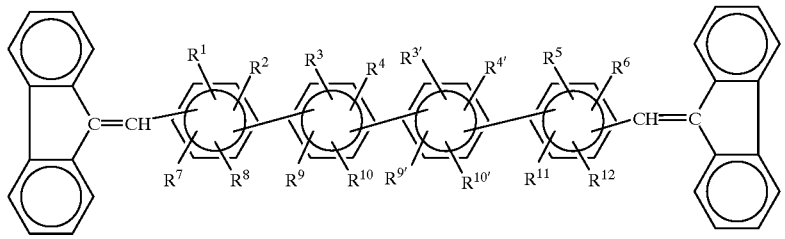

As those where X and Y form a saturated 6-membered ring, mentioned are the following compounds:

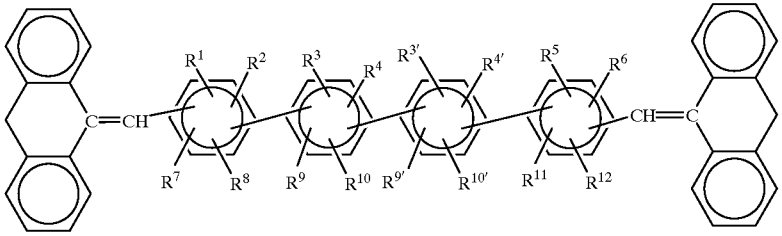

In the invention, the organic blue-emitting layer must indispensably have a glass transition temperature of not lower than 75° C. Therefore, the organic host compounds to be in the layer are preferably selected from those of the following general formula (II) in which the central polyphenylene skeletons are all bonded to the adjacent ones at their para-positions:

(II)

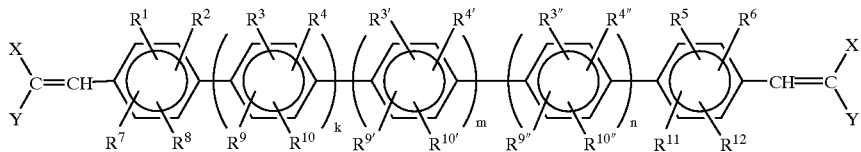

wherein $R^1$ to $R^{12}$, $R^{3'}$, $R^{4'}$, $R^{9'}$, $R^{10'}$, $R^{3''}$, $R^{4''}$, $R^{9''}$, $R^{10''}$, X, Y, k, m and n have the same meanings as above.

The styryl compounds of formula (I) can be produced by various known methods. For producing these, for example, mentioned are the following three methods. Method 1:

A phosphonate of a general formula (a):

(a)

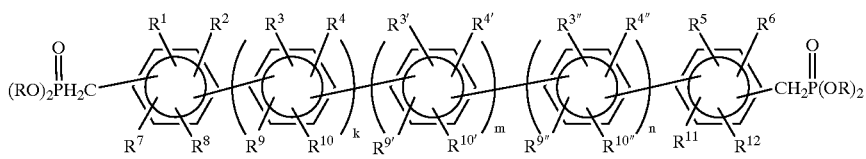

wherein k, m and n each are 0 or 1, and $(k+m+n) \geq 1$; $R^1$ to $R^{12}$, $R^{3'}$, $R^{4'}$, $R^{9'}$, $R^{10'}$, $R^{3''}$, $R^{4''}$, $R^{9''}$ and $R^{10''}$ have the same meanings as above; and R represents an alkyl group having from 1 to 4 carbon atoms, or a phenyl group, is condensed with a carbonyl group of a general formula (b):

(b)

wherein X and Y have the same meanings as above, in the presence of a base through Wittig reaction or Wittig-Horner reaction to give styryl compounds of formula (I) Method 2:

A dialdehyde compound of a general formula (c):

is condensed with a phosphonate of a general formula (d):

(d)

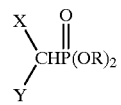

wherein R, X and Y have the same meanings as above, in the presence of a base through Wittig reaction or Wittig-Horner reaction to give styryl compounds of formula (I)

As the reaction solvent for that condensation, preferred are hydrocarbons, alcohols, and ethers. Specific examples of the solvent are methanol, ethanol, isopropanol, butanol, 2-methoxyethanol, 1,2-dimethoxyethane, bis(2-methoxyethyl) ether, dioxane, tetrahydrofuran(THF), toluene, and xylene. Also preferably employed are dimethylsulfoxide, N,N-dimethylformamide, (c)

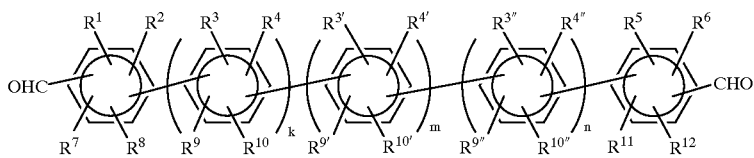

wherein k, m and n each are 0 or 1, and $(k+m+n) \geq 1$; and $R^1$ to $R^{12}$, $R^{3'}$, $R^{4'}$, $R^{9'}$, $R^{10'}$, $R^{3''}$, $R^{4''}$, $R^{9''}$ and $R^{10''}$ have the same meanings as above, N-methylpyrrolidone, 1,3-dimethyl-2-imidazolidinone, etc. Especially preferred are tetrahydrofuran and dimethylsulfoxide.

As the condensing agent, preferred are sodium hydroxide, potassium hydroxide, sodium amide, sodium hydride, n-butyl lithium, and even alcoholates such as sodium methylate, potassium t-butoxide, etc. Especially preferred are n-butyl lithium and potassium t-butoxide.

The reaction temperature varies, depending on the starting compounds to be reacted, and therefore cannot be defined indiscriminately. In general, however, it may be widely from 0° C. to about 100° C. Especially preferably, the reaction temperature falls between 0° C. and room temperature.

Method 3

A bromide of a general formula (e):

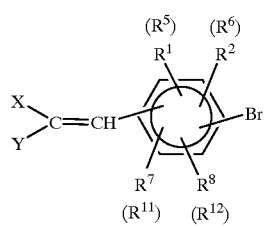

(e)

wherein X, Y, $R^1$, $R^2$, $R^7$, $R^8$, and also $R^5$, $R^6$, $R^{11}$ and $R^{12}$ have the same meanings as above, is reacted with Mg to give a Grignard reagent, which is coupled with a dibromoarylene compound of a general formula (f):

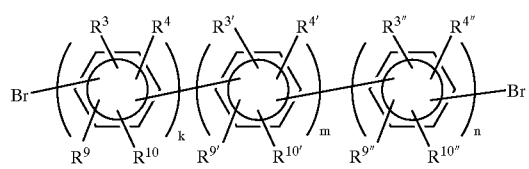

(f)

wherein k, m and n each are 0 or 1, and (k+m+n)≧1; and $R^3$, $R^4$, $R^9$, $R^{10}$, $R^{3'}$, $R^{4'}$, $R^{9'}$, $R^{10'}$, $R^{3''}$, $R^{4''}$, $R^{9''}$ and $R^{10''}$ have the same meanings as above, in the presence of a metal catalyst to give styryl compounds of formula (I).

As the metal catalyst for the coupling, employable is a transition metal complex catalyst. Preferred are nickel catalysts and palladium catalysts, which include, for example, $NiCl_2$ (dppp) (Tokyo Kasei), $[NiCl_2(PPh_3)_2]$, and also $PdCl_2$ (dppf), and $Pd(PPh_3)_4$.

As the reaction solvent, employable is any of dewatered diethyl ether, THF, di-n-propyl ether, di-n-butyl ether, di-i-propyl ether, diethylene glycol dimethyl ether (diglyme), dioxane, dimethoxyethane (DME), etc.

Preferred are diethyl ether and THF.

Specific examples (1) to (61) of the styryl compounds for use in the invention are mentioned below, which, however, are not intended to restrict the scope of the invention.

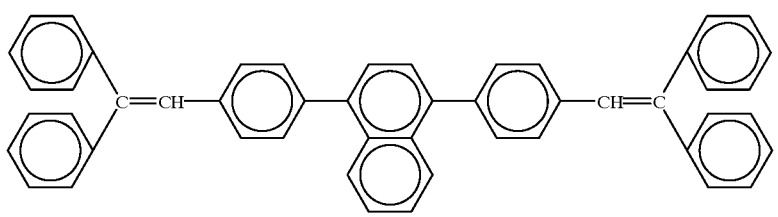

(1)

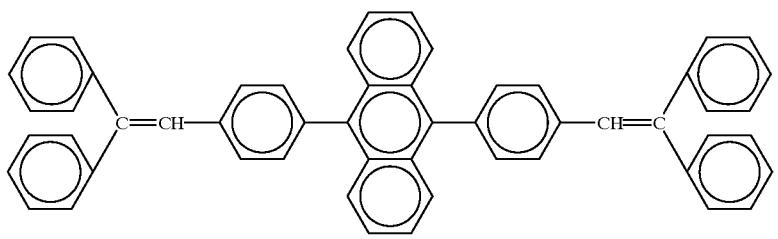

(2)

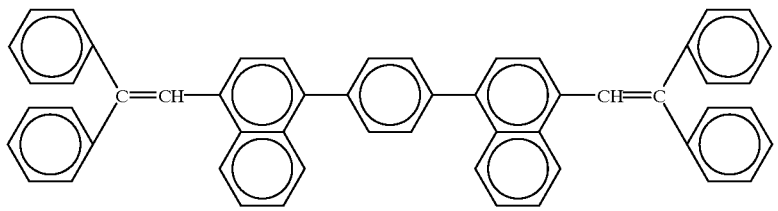

(3)

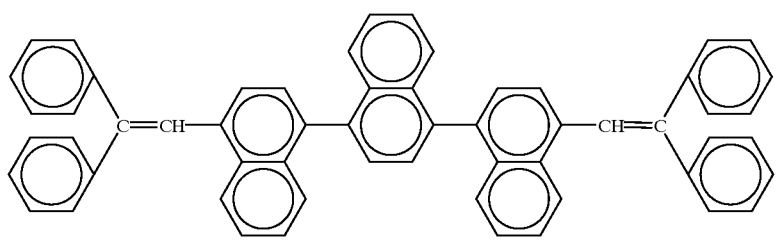
(4)
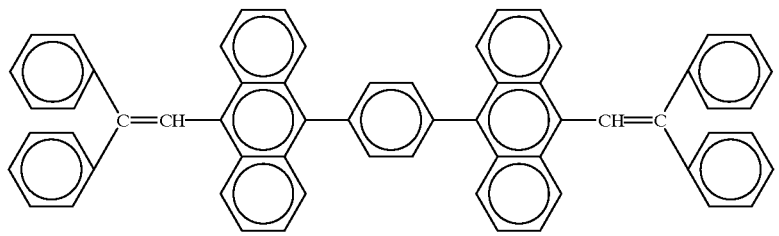
(5)
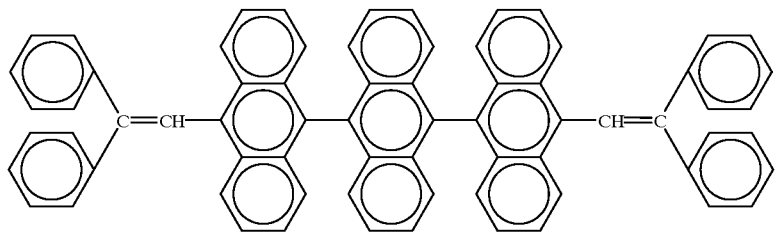
(6)
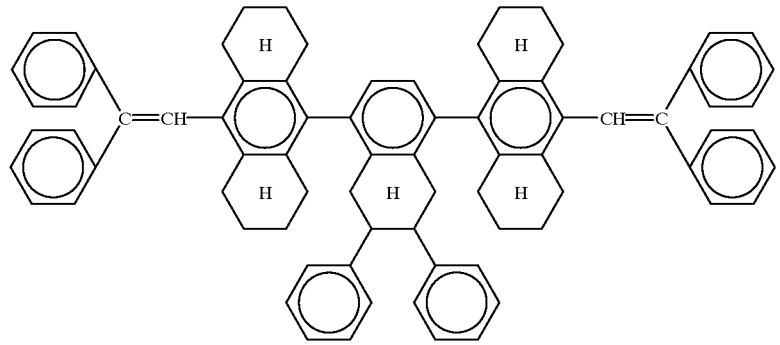
(7)
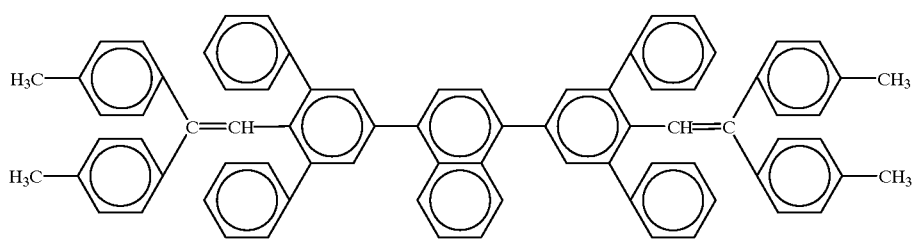
(8)

-continued
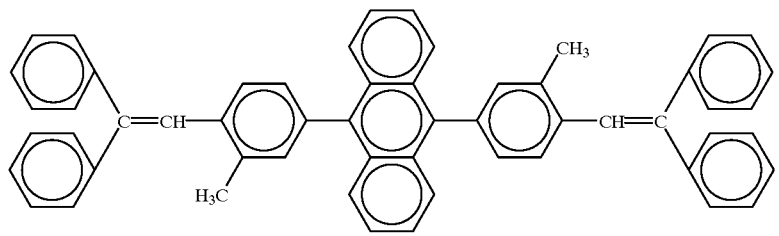
(9)
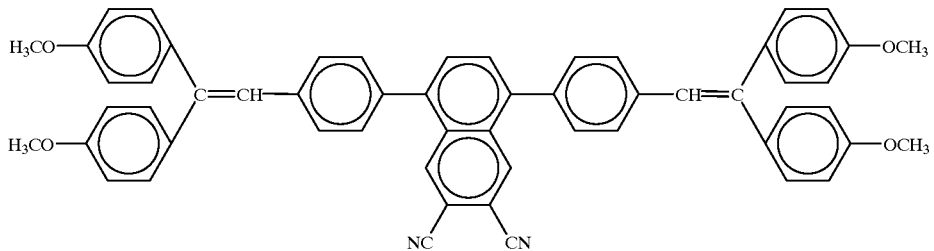
(10)
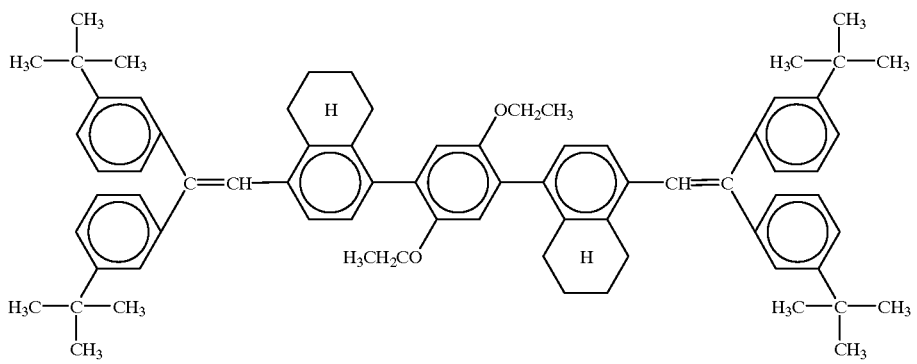
(11)
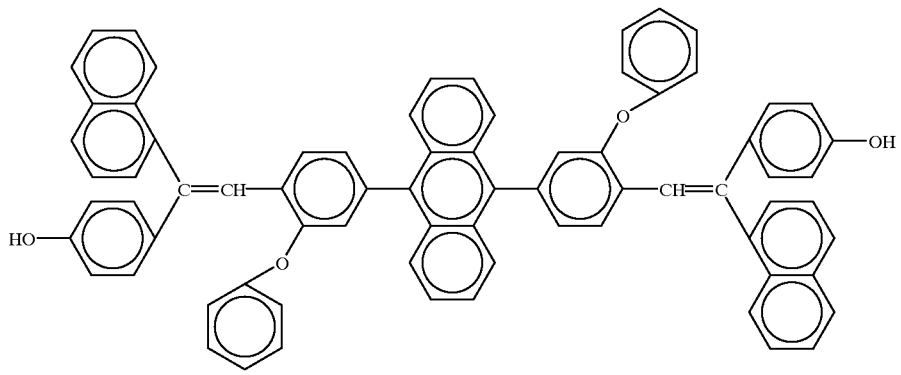
(12)
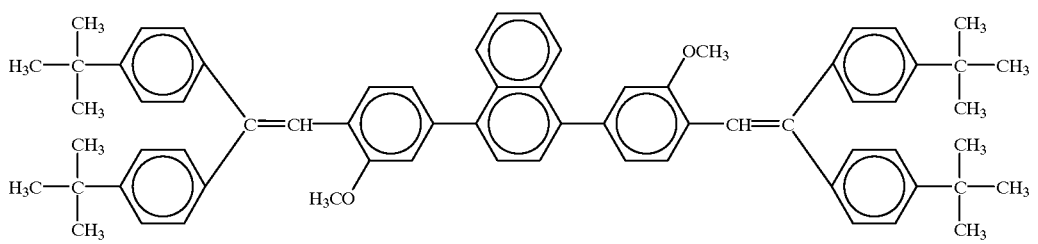
(13)

(14)
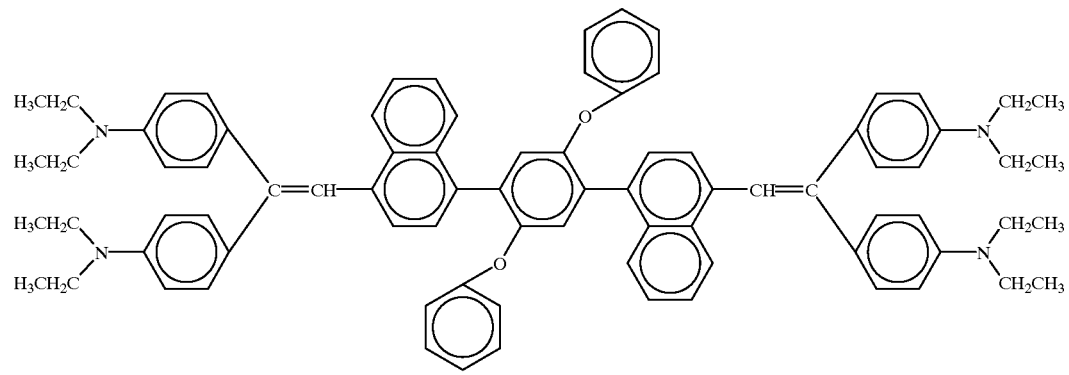
(15)
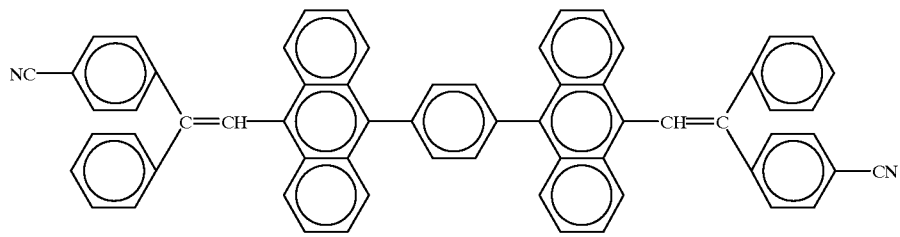
(16)
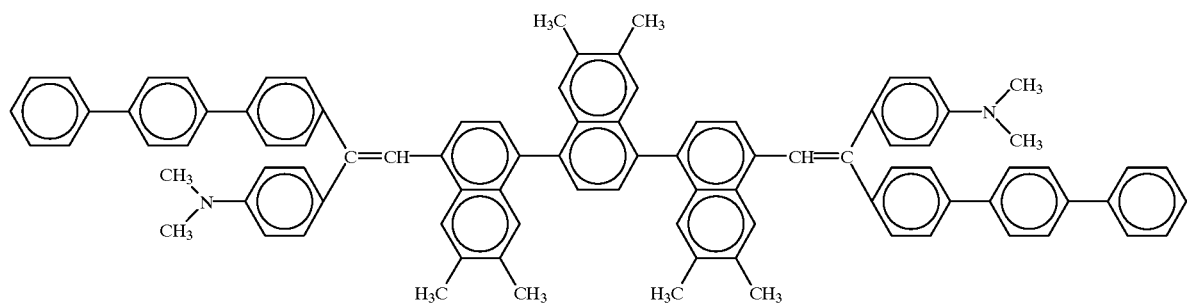
(17)
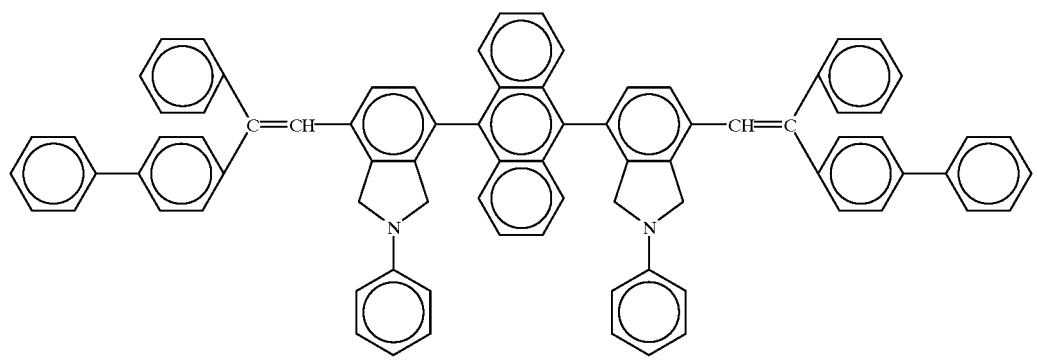

-continued
(18)
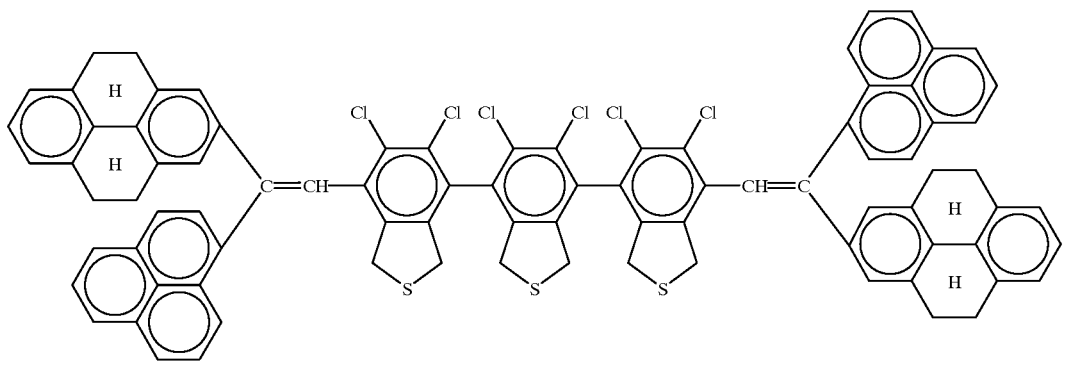
(19)
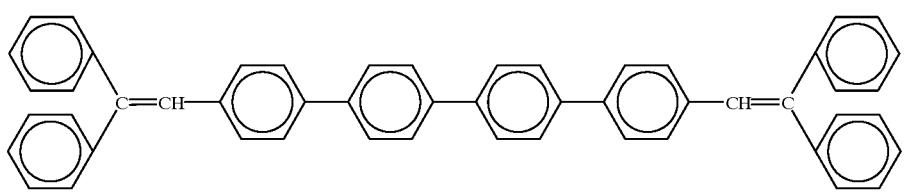
(20)
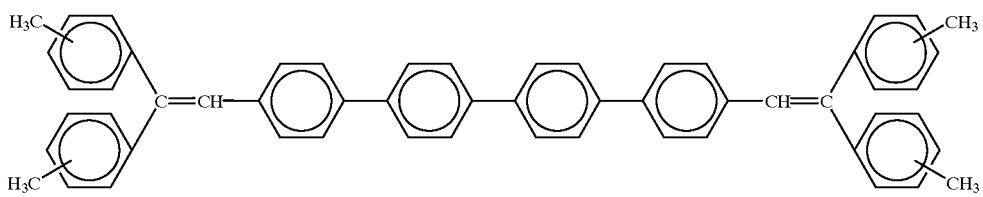
(21)
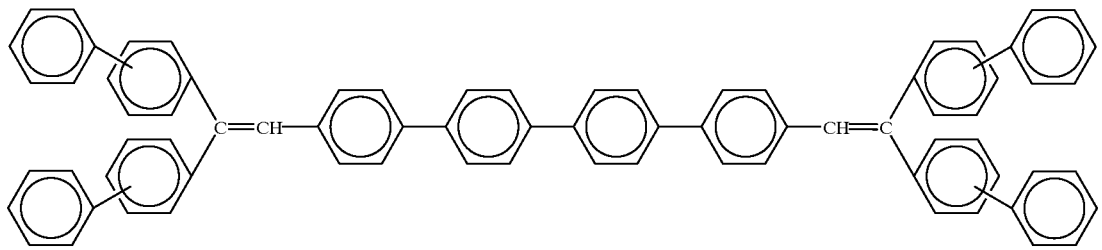
(22)
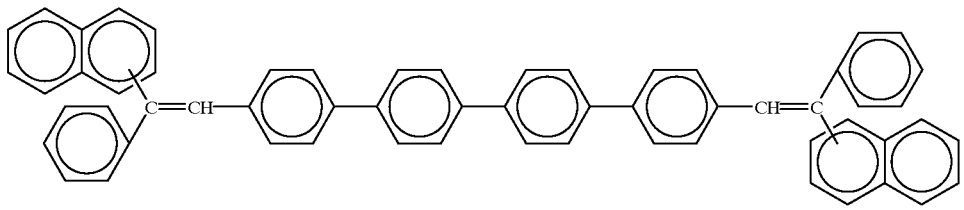

(23)
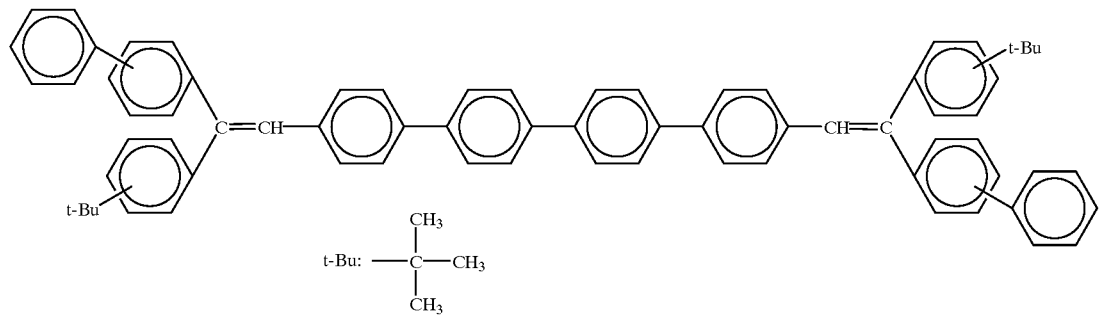
(24)
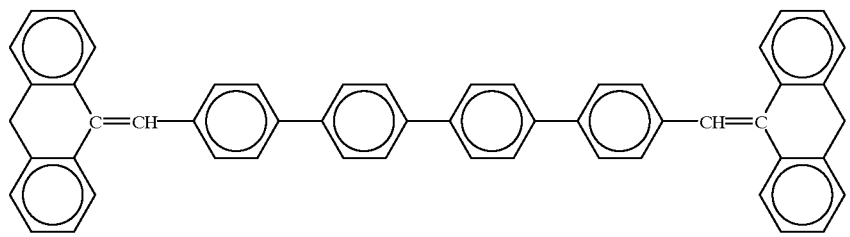
(25)
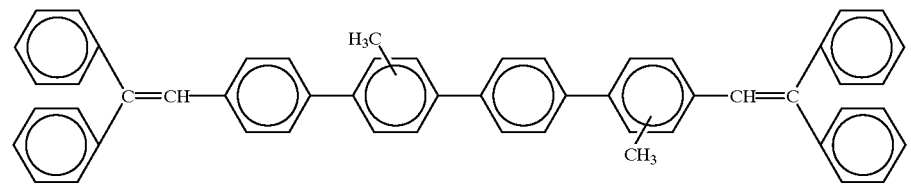
(26)
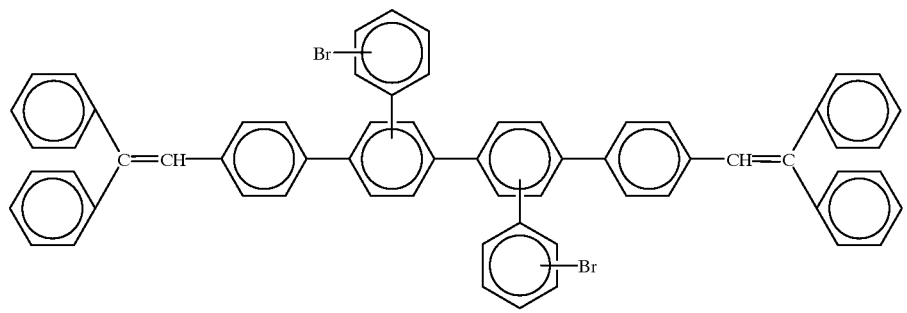
(27)
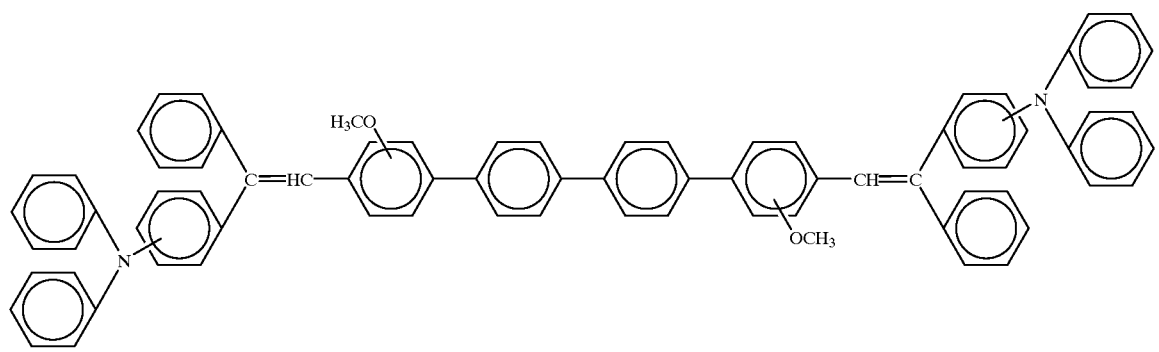

(28)
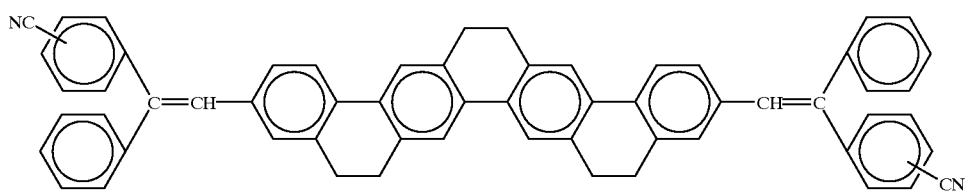
(29)
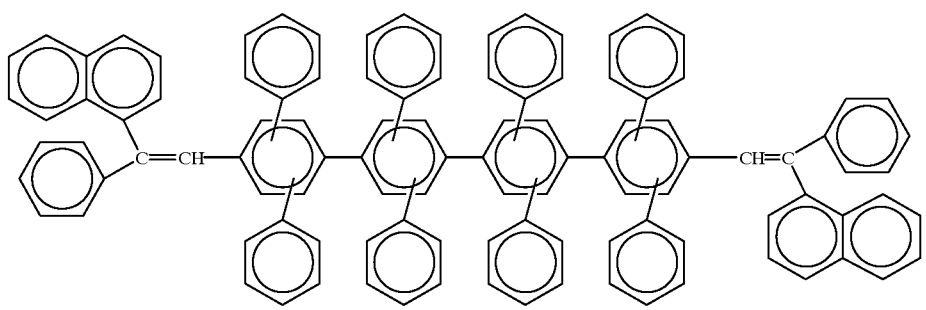
(30)
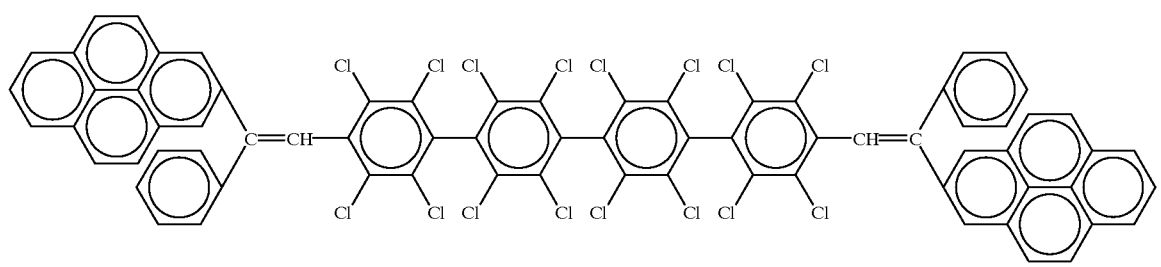
(31)
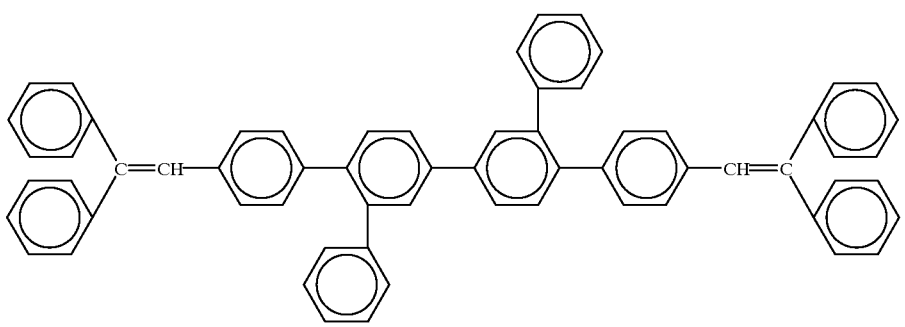
(32)
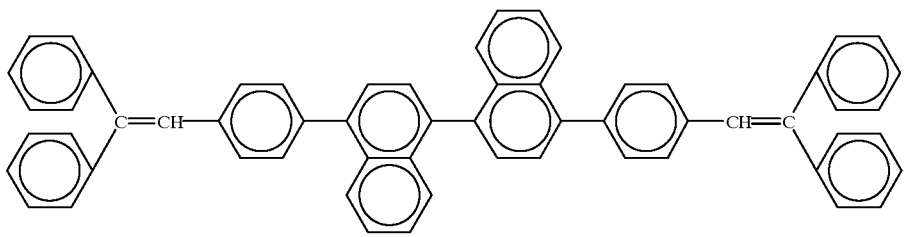

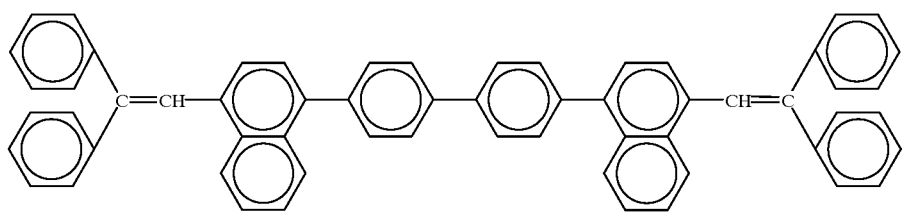
(33)
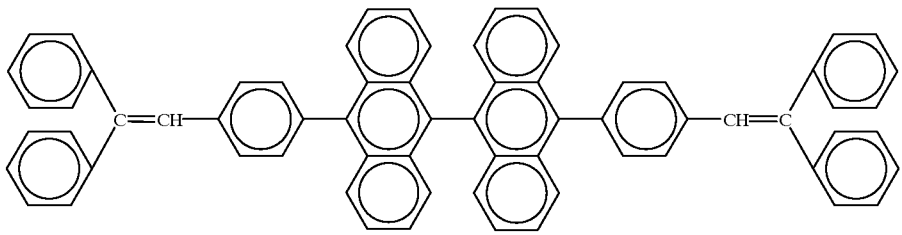
(34)
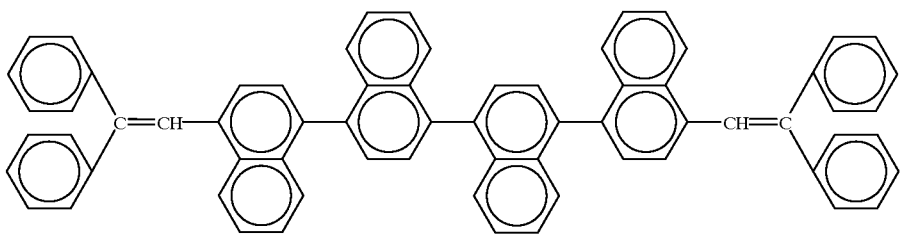
(35)
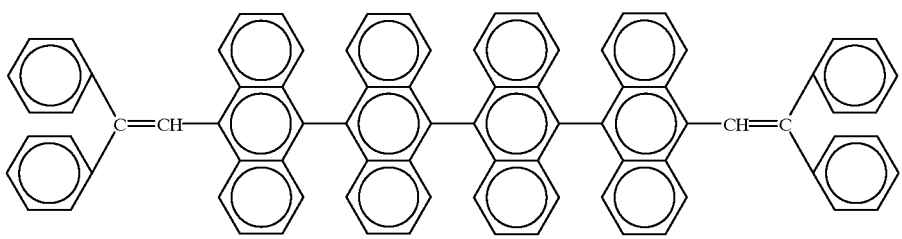
(36)
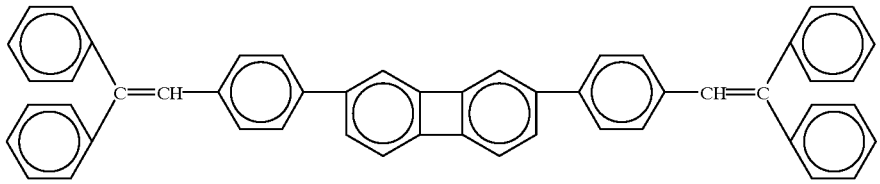
(37)
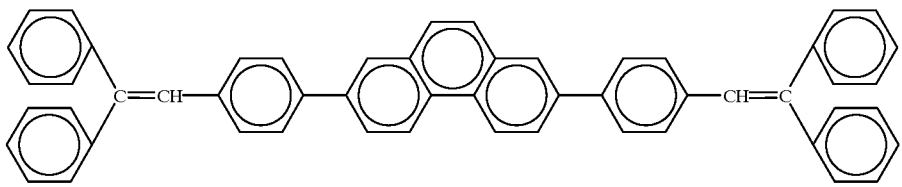
(38)

(39)
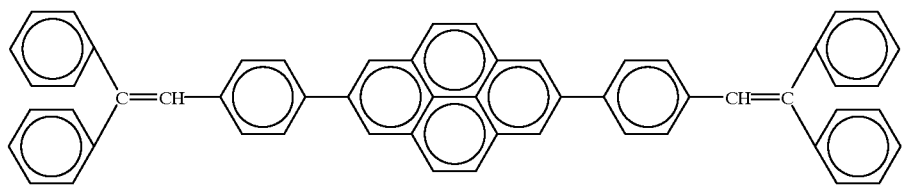
(40)
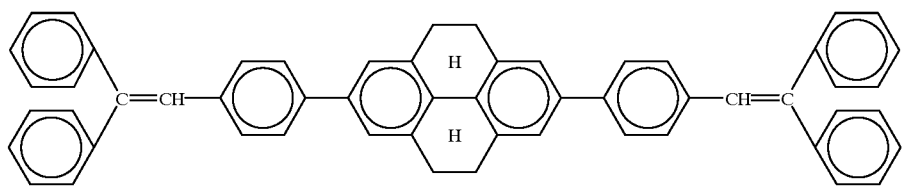
(41)
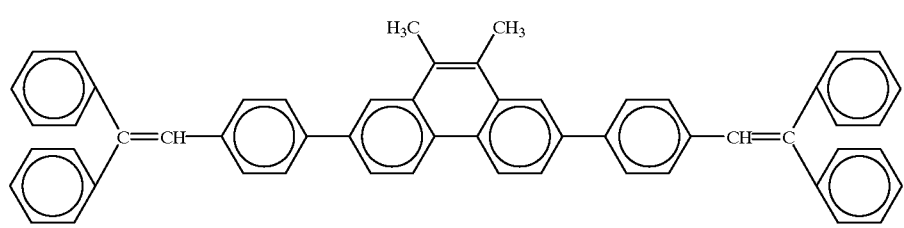
(42)
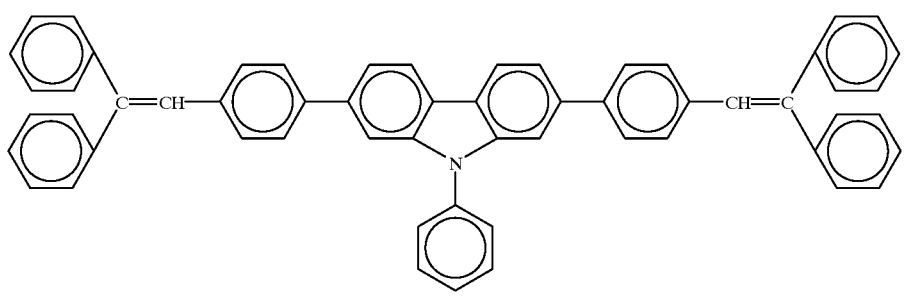
(43)
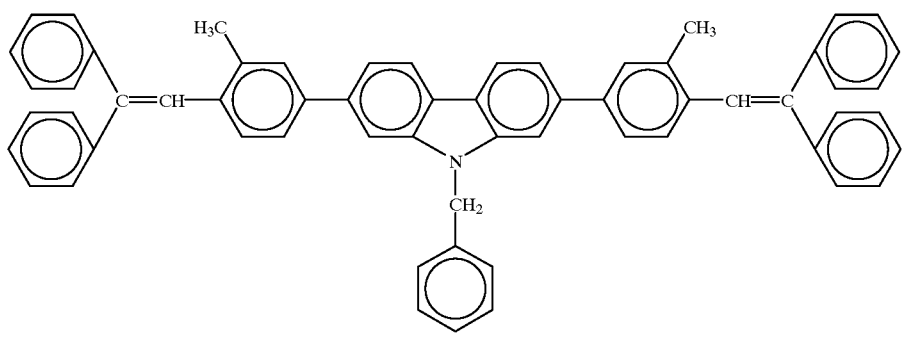

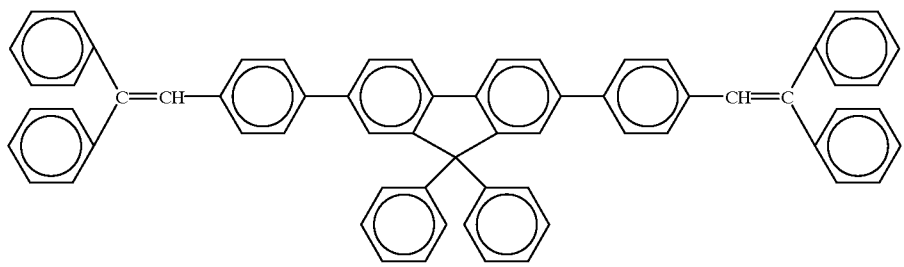
(44)
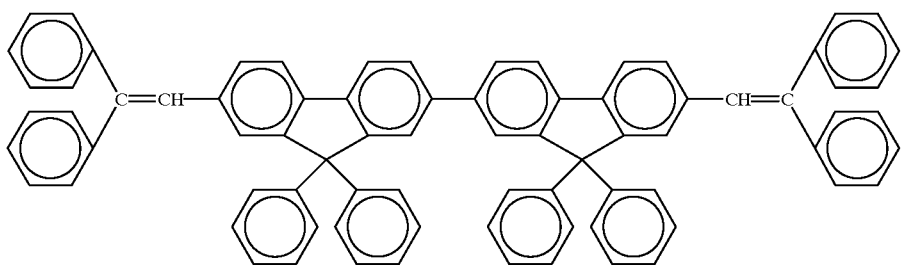
(45)
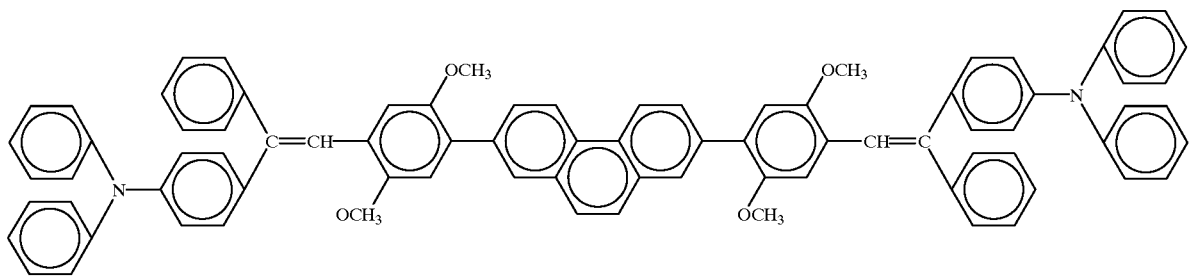
(46)
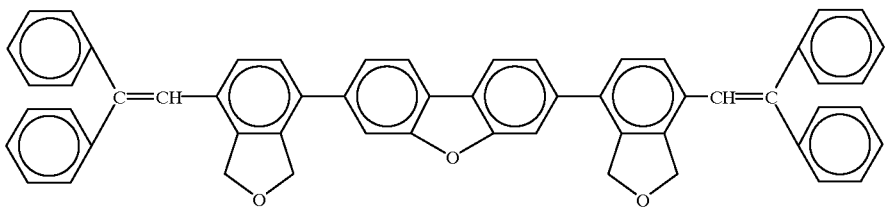
(47)
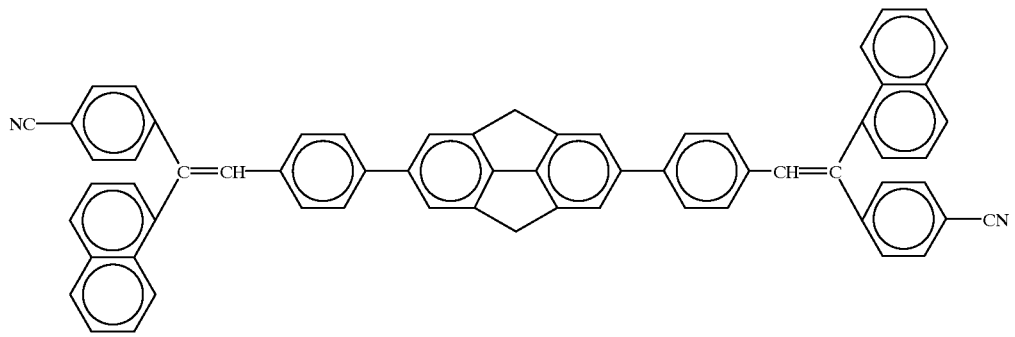
(48)

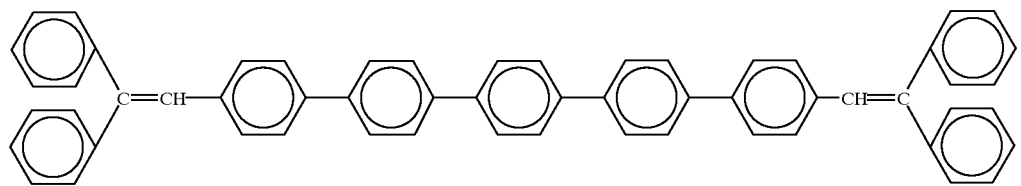
(49)
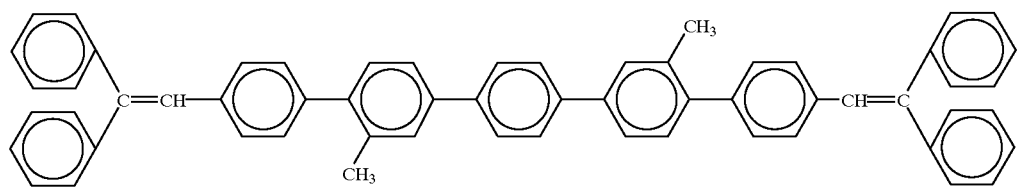
(50)
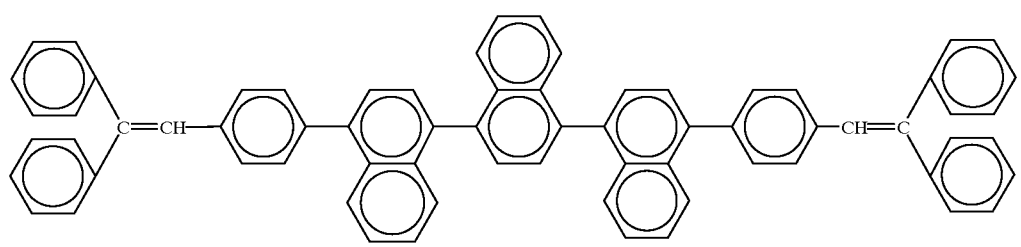
(51)
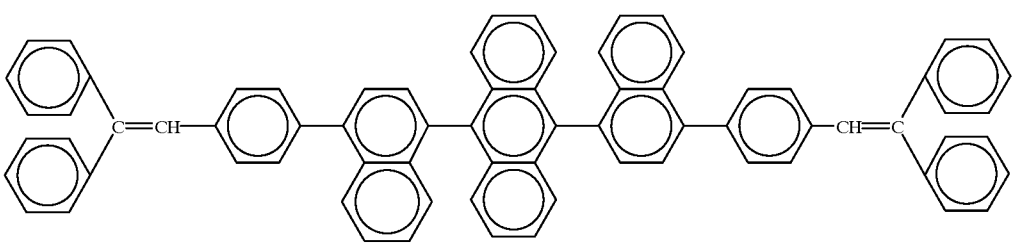
(52)
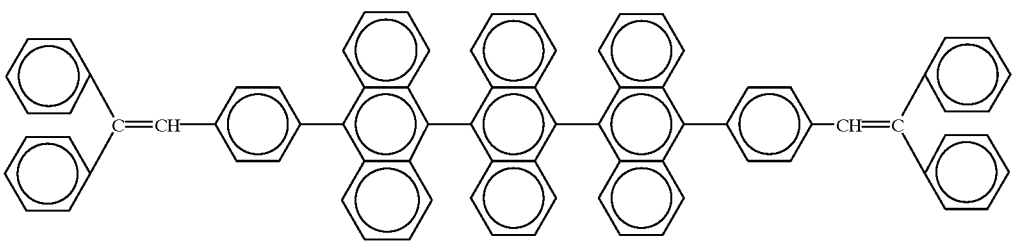
(53)
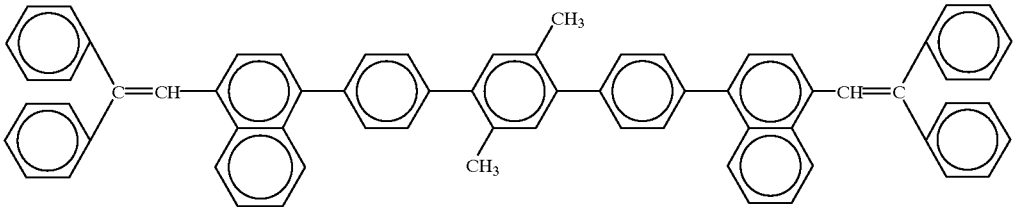
(54)

(55)
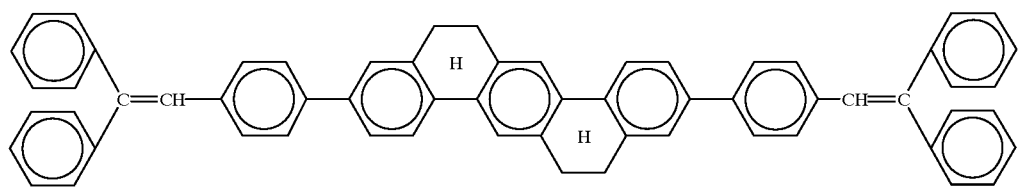
(56)
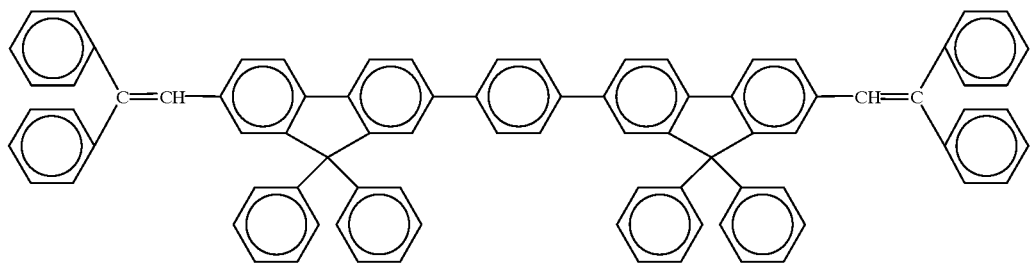
(57)
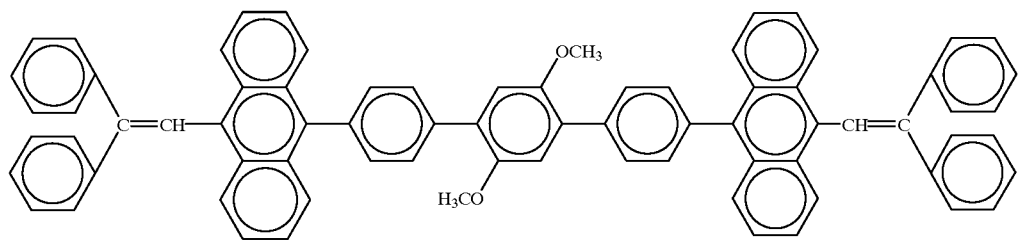
(58)
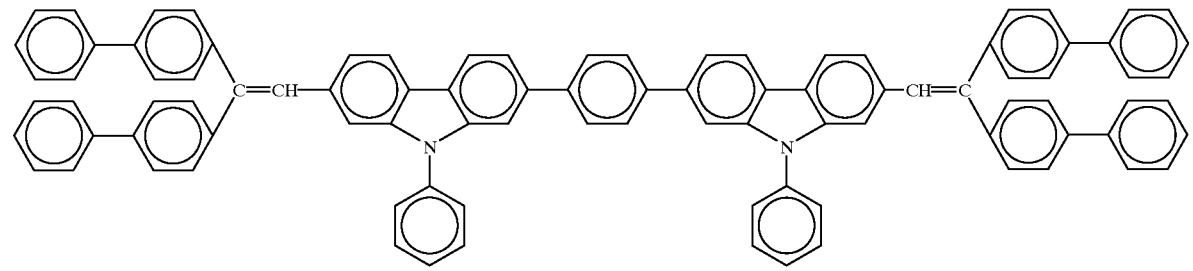
(59)
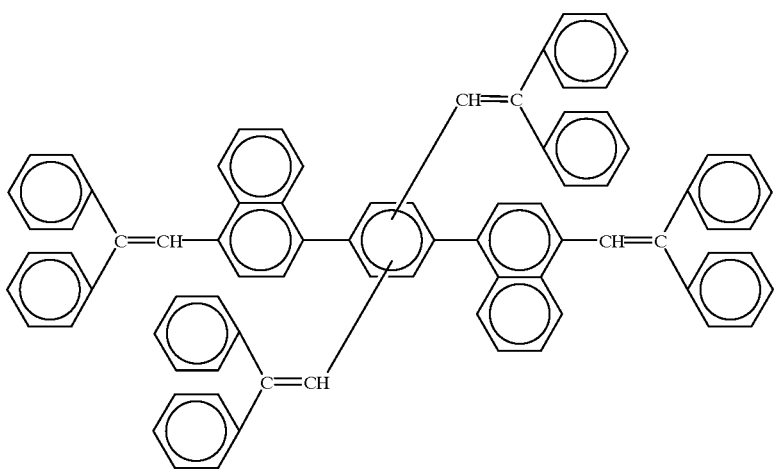

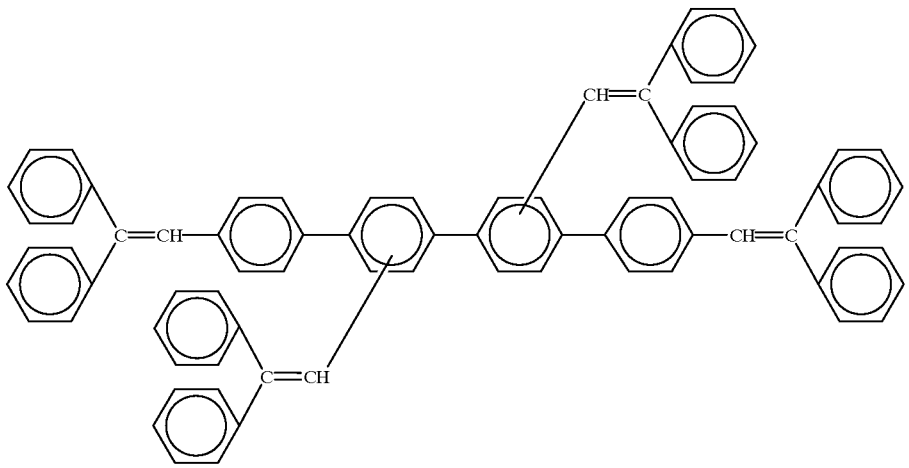

(60)

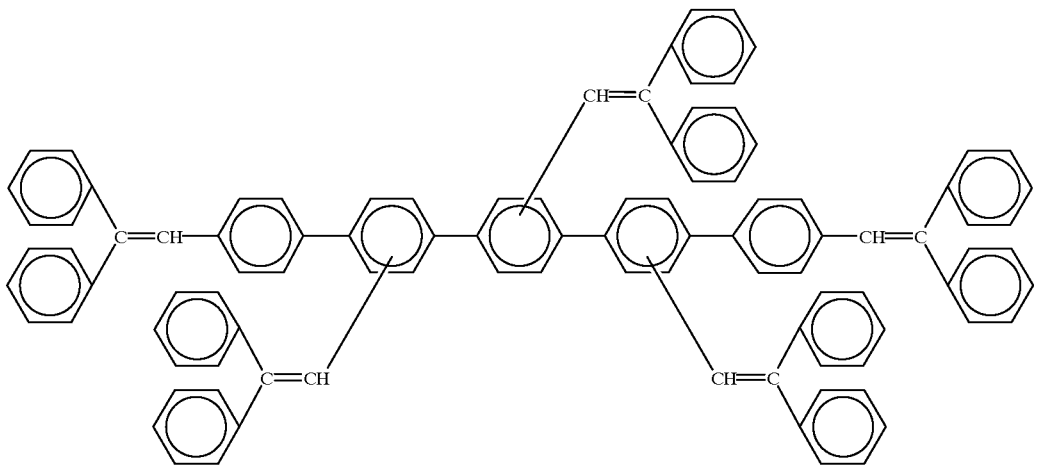

(61)

In the invention, one or more of those organic host compounds may be used either singly or as combined.

The fluorescent substance which is the other component constituting the organic blue-emitting layer is doped into the organic light-emitting layer in order to improve the efficiency of the organic EL device and to prolong the life thereof. The fluorescent substance is not specifically defined, provided that it can emit light in response to the recombination of holes and electrons, and may be any known fluorescent dye. However, it is important that the fluorescent substance is so selected that its energy gap is smaller than the energy gap of the organic host compound. The fluorescent substance includes, for example, stilbene derivatives, tristyrylarylene derivatives, and distyrylarylene derivatives (see Japanese Patent Application Laid-Open No. 5-129438). In the invention, one or more such fluorescent substances can be used either singly or as combined.

The organic host compound and the fluorescent substance are suitably selected and combined to give the organic blue-emitting layer, in which the efficient energy transfer from the organic host compound to the fluorescent substance is realized to attain the improvement in the efficiency of the organic EL device and the prolongation of the life thereof. In that preferred case, it has been found that the profile of the EL spectrum quite agrees with that of the fluorescence spectrum of the fluorescent substance within a range of ±10 nm with respect to the fluorescence peak wavelengths and the individual peak wavelengths of the vibronic structure. The fluorescence spectrum of the fluorescent substance is measured in a solution of the fluorescent substance as dissolved in a non-polar solvent such as toluene. When the profile of the EL spectrum quite agrees with that of the fluorescence spectrum of the fluorescent substance, it is herein referred that the EL device has "monomeric light-emitting ability".

In the organic EL device of the invention having the monomeric light-emitting ability, it is meant that the initial state of EL corresponds to the excited monomeric state of the fluorescent substance in the organic light-emitting layer.

In order to improve the luminous efficiency of the organic EL device, it is effective to increase the fluorescence quantum efficiency of the organic host compound in the device. In the invention, therefore, that quantum efficiency must be not smaller than 0.3. The fluorescence quantum efficiency of the organic host compound is measured in a thin film of the substance, and is different from that as measured in its solution.

The organic EL device of the invention must retain a monomeric blue-emitting ability. Therefore, the organic host compound and the fluorescent substance are selected such that the interaction between the organic host compound and the fluorescent substance is absent and the interaction between the organic host compound and the adjacent compound layers is absent. As for blue-emitting organic host compounds, the interaction between the organic host compound and the fluorescent substance existing in the emitting layer and the interaction between the organic host compound and the adjacent organic compound layers are often large in many cases, in those cases the state having energy smaller than the energy of an excited state of the fluorescent substance is formed (an exciplex). As a result, in those cases, the energy of the excited state of the fluorescent substance is transferred to the state having smaller energy, whereby the EL device gives a broad emission spectrum which, being different from the fluorescence spectrum of the monomeric emission from the fluorescent substance, has peaks at longer wavelengths. Even if the EL devices of those cases could produce monomeric emission in the initial stage of their driving, the light as emitted by them will often become different from monomeric one while the devices are continuously driven for long. Such EL devices that could not retain the ability of monomeric emission shall have an extremely short life.

Therefore, in the organic EL device of the invention, it is extremely important to select the combination of the organic host compound and the fluorescent substance so that the device can retain the ability of monomeric emission.

In addition, all the organic compound layers constituting the organic EL device of the invention must have a glass transition temperature of not lower than 75° C., in order to make the device have good heat resistance. Moreover, in order to further improve the storage stability of the device at 75° C., the stability of the interfaces between the organic light-emitting layer and the adjacent organic compound layers is an important factor. Therefore, the organic compound layers adjacent to the organic light-emitting layer must have a glass transition temperature of not lower than 105° C. If satisfying those requirements, the organic EL device is free from the change in the color to be emitted by it and from the reduction in the efficiency of the device, while maintaining its good properties for long, even though stored in a high-temperature atmosphere at 75° C.

The layer constitution of the organic EL device of the invention is not specifically defined, and may be any desired one. Basically, however, the organic blue-emitting layer is sandwiched between a pair of electrodes (positive electrode and negative electrode), in which are optionally provided a hole injection and transportation layer and an electron injection layer. Those are formed on a transparent substrate, through which the light emitted is seen. Examples of the organic EL device having that layer constitution are mentioned below.

(1) Positive electrode/organic light-emitting layer/ negative electrode (2) Positive electrode/hole injection layer/organic light-emitting layer/negative electrode (3) Positive electrode/organic light-emitting layer/ electron injection layer/negative electrode (4) Positive electrode/hole injection layer/organic light-emitting layer/electron injection layer/negative electrode (5) Positive electrode/hole injection layer/hole transportation layer/organic light-emitting layer/electron injection layer/negative electrode In these structures, the organic compound layers such as the hole injection layer, the hole transportation layers and the electron injection layer are not specifically defined, provided that they satisfy the requirements for their glass transition temperature.

The organic EL device of the invention is optionally provided with a hole injection and transportation layer, which functions to inject holes thereinto from the positive electrode and to transport them into the light-emitting layer. Preferably, the hole injection and transportation layer has a hole mobility of not smaller than $10^{-6}$ cm²/V·s in an electric field of from $10^4$ to $10^6$ V/cm. If desired, the organic EL device may be provided with a laminate of a hole injection layer and a hole transportation layer.

The material to be in the hole injection and transportation layer may be selected from, for example, compounds of a general formula (III):

(III)

In formula (III), $Q^1$ and $Q^2$ each represent a group having a nitrogen atom and at least three carbon rings (of which at least one is an aromatic ring such as a phenyl group), and these maybe the same or different; G represents a cycloalkylene group, an arylene group, or a linking group comprising a carbon-carbon bond.

In the organic EL device of the invention, the hole injection layer and the hole transportation layer that are directly adjacent to the organic light-emitting layer must have a glass transition temperature of not lower than 105° C. Therefore, the materials of those layers are preferably selected from oligomer amines of the compounds of formula (III) comprising three or more arylamines as bonded in a linear or branched manner.

The compounds of that type are, for example, represented by the following general formula (IV):

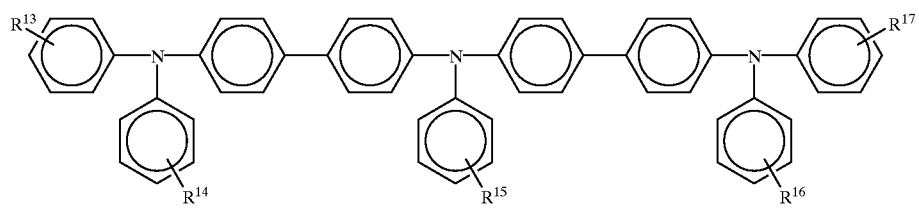

(IV)

wherein $R^{13}$ to $R^{17}$ each represent an alkyl group, an alkoxy group or a phenyl group, and may be the same or different, the phenyl substituent being optionally condensed with the group on which it is substituted to give a naphthyl group.
Specific examples of the compounds are mentioned below.
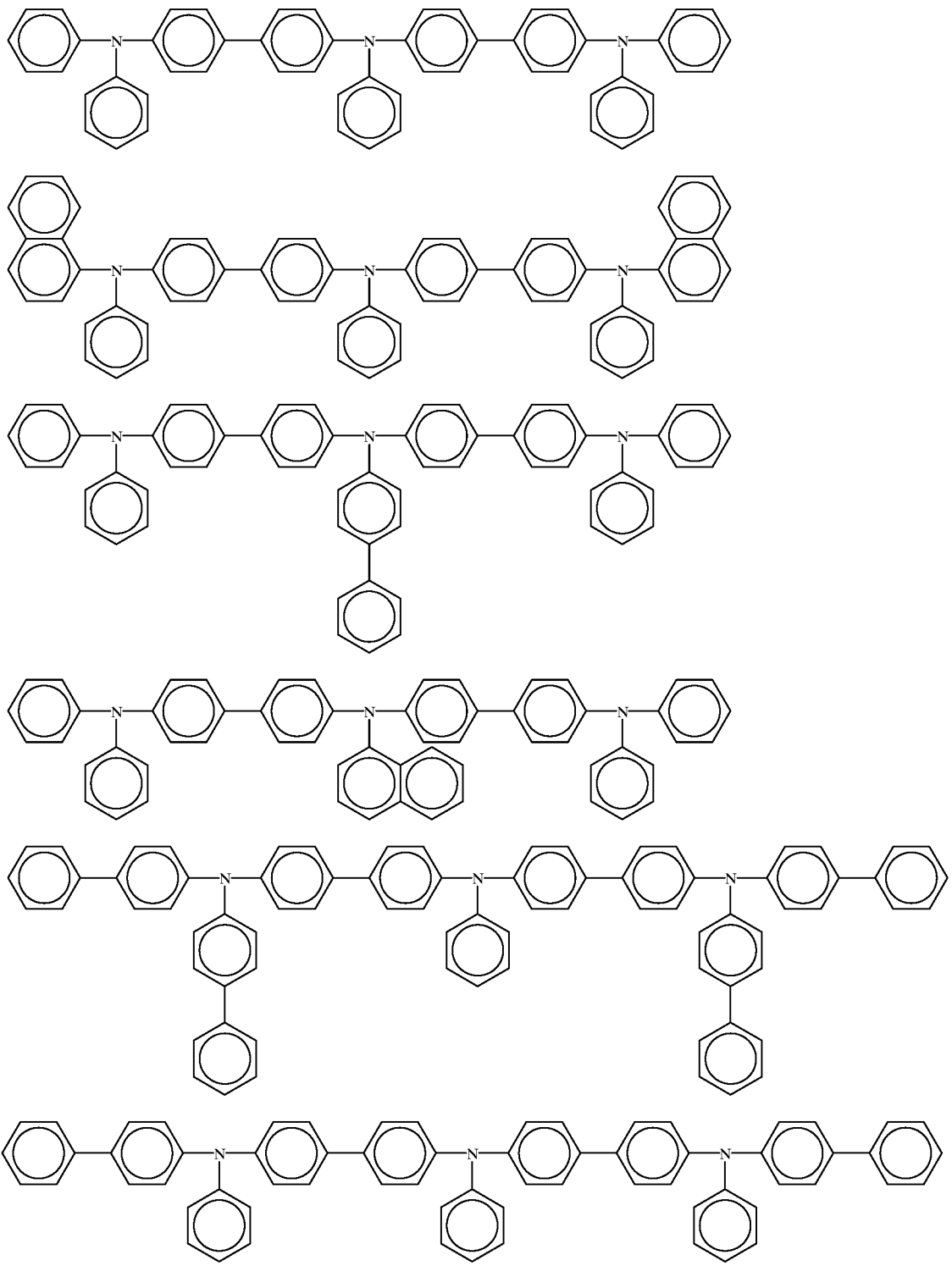

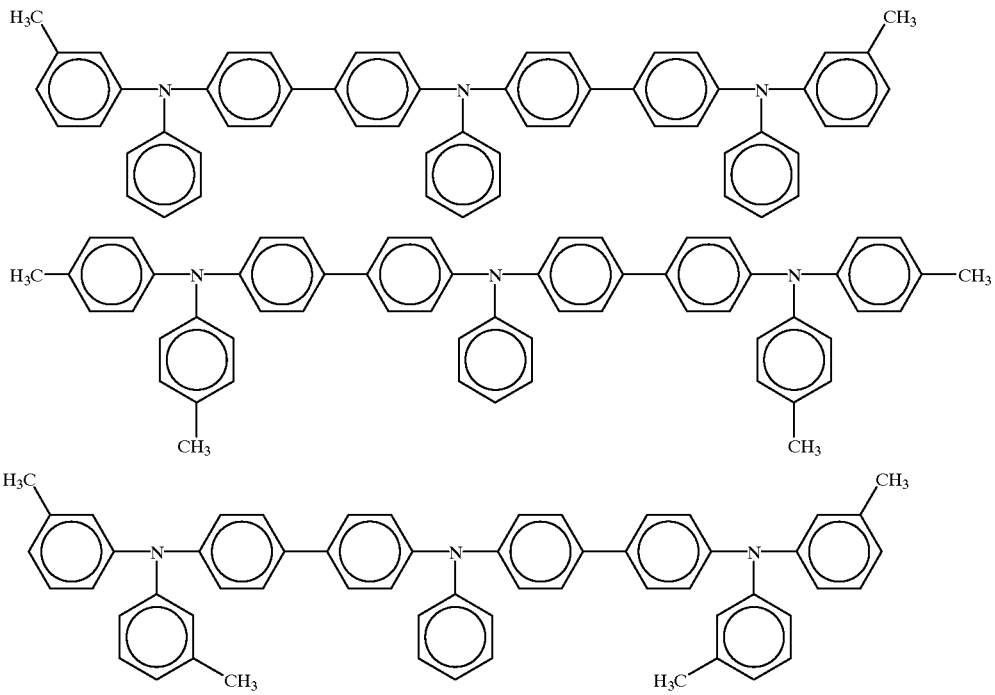

The layers may comprise one or more of those compounds either singly or as combined.

The organic EL device of the present invention is optionally provided with an electron injection layer (electron injection and transportation layer), which functions to transfer the electrons as injected thereinto from the negative electrode to the organic light-emitting layer, and may comprise any known conventional electron-transmitting compound. For example, the material to be in the layer is preferably selected from metal complexes of 8-hydroxyquinoline or its derivatives, or oxadiazole derivatives.

As examples of metal complexes of 8-hydroxyquinoline or its derivatives, mentioned are metal chelate oxanoid compounds containing chelates of oxine (generally, 8-quinolinol or 8-hydroxyquinoline), etc. Compounds of that type all have a glass transition temperature of not lower than 105° C.

The electron injection layer may comprise one or more of those compounds either singly or as combined.

Preferably, the organic EL device of the invention having the constitution mentioned above is supported by a substrate, and the substrate in this use is not specifically defined. Any ordinary substrate for conventional organic EL devices is employable herein. For example, employed is any of glass or transparent plastics.

The positive electrode constituting the organic EL device of the invention is to inject holes into the device. For this, preferred are electrode materials having a large work function (not smaller than 4 eV), such as metals, alloys, electroconductive compounds and their mixtures. Specific examples of such preferred electrode materials are metals such as Au, and electroconductive transparent materials such as CuI, ITO (indium tinoxide), $SnO_2$, ZnO, etc. The positive electrode can be formed, for example, through vacuum vapor deposition or sputtering of such an electrode material to give a thin film. For light emission through the electrode, it is preferred that the electrode has a transmittance, relative to the light emitted, of not smaller than 10%, and that the sheet resistance of the electrode is not larger than hundreds of ohms per square ($\Omega/\square$).

The thickness of the electrode film may be generally between 10 nm and 1 μm, preferably between 50 and 200 nm, depending on the material of the electrode.

The negative electrode constituting the organic EL device of the invention is to inject electrons into the device. For this, preferred are electrode materials having a small work function (not larger than 4 eV), such as metals, alloys, electroconductive compounds and their mixtures. Specific examples of such preferred electrode materials are sodium, sodium/potassium alloys, magnesium, lithium, magnesium/copper mixtures, magnesium/silver alloys, aluminium/lithium alloys, $Al/Al_2O_3$ mixtures, indium, rare earth metals, etc. The negative electrode can be formed, for example, through vacuum vapor deposition or sputtering of such an electrode material to give a thin film. For light emission through the electrode, it is preferred that the electrode has a transmittance, relative to the light emitted, of not smaller than 10%, and that the sheet resistance of the electrode is not larger than hundreds of ohms per square ($\Omega/\square$). The thickness of the electrode film may be generally between 10 nm and 1 μm, preferably between 50 and 200 nm, depending on the material of the electrode.

Now, preferred embodiments of producing the organic EL device of the invention are referred to hereinunder. First, a thin film of a desired electrode material, for example, a positive electrode material is formed on a suitable substrate through vapor deposition or sputtering to have a thickness of from 50 to 200 nm. This is formed a positive electrode on the substrate. Next, thin films of a hole injection layer, a hole transportation layer, an organic blue-emitting layer, and an electron injection layer are formed on the positive electrode.

To form those thin films, for example, employable is any of spin-coating, casting or vapor deposition. Preferred is vacuum vapor deposition, through which uniform films with few pin holes are easy to obtain. For the vapor deposition to form those thin films, the condition varies, depending on the type of the compound to be vaporized for the deposition, and the intended crystal structure and association structure of the molecular film to be deposited, but is preferably such that the boat heating temperature falls between 50 and 400° C., the vacuum degree falls between $10^{-6}$ and $10^{-3}$ Pa, the deposition rate falls between 0.01 and 50 nm/sec, the substrate temperature falls between −50 and 300° C., and the film thickness falls between 5 nm and 5 μm.

After the formation of those layers, a thin film of a negative electrode material is formed thereover, for example, through vapor deposition or sputtering to be a negative electrode having a film thickness of from 10 nm to 1 μm, preferably from 50 to 200 nm. Thus is produced the intended organic EL device. To produce the device, the order of forming the electrodes and the layers may be reversed.

Where a direct current voltage is applied to the organic EL device thus produced in that manner, a voltage of from 3 to 40 V or so may be applied thereto with its positive electrode being charged to be plus (+) and its negative electrode to be minus (−), whereby the device emits blue. Even if the same voltage is applied to the device in the reversed manner relative to the polarity of the electrodes, the device emits no light. Where an alternating current is applied to the device, the device emits light only when its positive electrode is charged to be plus (+) and its negative electrode to be minus (−). The wave mode of the alternating current to be applied to the device may be any desired one.

Now, the invention is described in more detail with reference to the following Examples, which, however, are not intended to restrict the scope of the invention.

EXAMPLE 1

(1) Production of Organic EL Device

A member comprising a 25 mm×75 mm×1.1 mm glass substrate and a 120 nm thick film electrode of ITO provided on the glass substrate was used as a transparent substrate. This was ultrasonically washed with isopropyl alcohol for 5 minutes, then washed with pure water for 5 minutes, and finally again ultrasonically washed with isopropyl alcohol for 5 minutes. Next, isopropyl alcohol was removed from the surface of the substrate by applying a dry nitrogen stream thereonto, and the substrate was then cleaned with ultraviolet rays with ozone.

This transparent substrate was mounted onto a substrate holder of a commercially-available vacuum vapor deposition system (manufactured by Nippon Vacuum Technology Co.). Five electrically-heating molybdenum boats were prepared, each of which was loaded with any of 500 mg of 4,4'-bis[N,N-di(m-tolyl)amino]-4"-phenyl-triphenylamine (TPD74), 500 mg of 4,4'-bis[N-phenyl-N-(1-naphthyl)-4-aminophenyl]triphenylamine (TPD78), 500 mg of 9,10-di[4-(2,2'-diphenylvinyl-1-yl)phenyl]anthracene (DPVDPAN), 500 mg of 4,4'-bis[2-(4-(N,N-diphenylamino)phenyl)vinyl]biphenyl (DPAVBi), and 100 mg of tris(8-hydroxyquinoline)aluminium (Alq).

The vacuum chamber of the system was degassed to have a reduced pressure of $1\times10^{-4}$ Pa, in which the boat loaded with TPD74 was heated whereby TPD74 was deposited on the substrate to form thereon a hole injection layer having a thickness of 60 nm. Next, the boat loaded with TPD78 was heated to vaporize TPD78, whereby was formed a hole transportation layer having a thickness of 20 nm. Next, the boat laded with DPVDPAN and the boat loaded with DPAVBi were heated simultaneously to vaporize DPVDPAN and DPAVBi, whereby a light-emitting laminate layer having a thickness of 40 nm was formed on the hole transportation layer. The ratio by weight of DPVDPAN to DPAVBi in the light-emitting layer was 40/1. Finally, the boat loaded with Alq was heated to deposit Alq on the light-emitting layer, whereby was formed thereon an electron injection layer having a thickness of 20 nm.

Next, the sample thus produced was taken out of the vacuum chamber, and a mask of stainless steel was provided on the electron injection layer. This was again mounted onto the substrate holder, and a lithium/aluminium alloy matrix having a lithium concentration of 5 atm. %, from which is formed a negative electrode, was vaporized at a vacuum degree of $1\times10^{-4}$ Pa and at a deposition rate of from 0.5 to 1.0 nm/sec to thereby form a negative electrode having a thickness of 150 nm.

(2) Light Emission Test of Organic EL Device

A direct current of 6 V was applied to the device thus obtained, with its ITO electrode being charged to be positive and its Al—Li alloy electrode to be negative, whereupon the device emitted uniform blue light.

Regarding the initial characteristics of the device at a voltage of 6 V and a current density of 1.9 mA/cm$^2$, its luminance was 101 cd/m$^2$, and its electric power conversion efficiency (luminous efficiency) was high to be 2.8 lm/W. Observing the device with the naked eye and with a luminometer (CS-100, manufactured by Minolta Co.), any non-emitting points were found on the light-emitting surface of the device and the device emitted light uniformly.

The EL spectrum of the device exhibited a vibrational structure, for which the individual peak wavelengths were the same as those in the fluorescence spectrum of the dopant (DPAVBi) from its toluene solution within a range of ±10 nm. The fluorescence quantum efficiency of the organic host compound, DPVDPAN in its thin film was 0.4.

This device was driven in a constant current condition in a nitrogen stream at an initial luminance of 100 cd/cm$^2$, whereupon the half value period for it to have a luminance of 50 cd/cm$^2$ was 3000 hours. During the driving test, there was no change in the color of the light emitted by the device, and it was found that the device retained the ability of monomeric light emission.

(3) Heat Resistance Test of Organic EL Device

The device was cased in a glass housing, into which was put an inert liquid(perfluoroether), and sealed. The thus-sealed device was stored in a thermo-hygrostat testing system at 75° C. At regular intervals, this was taken out, and its luminance, chromaticity and luminous efficiency were measured. The data thus measured verified that the light emitted by the device did not change at all for 500 hours or longer, and the device was stable for such a long time. In addition, the luminous efficiency of the device did not also change. From those, it is understood that the storage life of the device at 75° C. is 500 hours or longer, and that the thermal stability of the device is very good.

The materials used for the organic compound layers had a glass transition temperature, Tg, of 80° C. (TPD74), 126° C. (TPD78), 105° C. (DPVDPAN), 180° C. (Alq). Thus, Tg of all those organic compound layers was higher than 75° C., and Tg of the organic compound layers (TPD78, Alq), between which the light-emitting layer was sandwiched, was not lower than 105° C.

The data obtained herein are shown in Table 1, along with those obtained in the following Comparative Examples.

Comparative Example 1

(1) Production of Organic EL Device:

An organic EL device was produced in the same manner as in Example 1, except that N,N'-diphenyl-N,N'-bis(1-naphthyl)-[1,1'-biphenyl]-4,4'-diamine (NPD) was used to form the hole transportation layer.

(2) Light Emission Test of Organic EL Device

Regarding the initial characteristics of the device at a voltage of 6 V and a current density of 1.9 mA/cm$^2$, its luminance was 100 cd/m$^2$, and its electric power conversion efficiency (luminous efficiency) was high to be 2.8 lm/W. Observing the device with the naked eye and with a luminometer (CS-100, manufactured by Minolta Co.), any non-emitting points were found on the light-emitting surface of the device and the device emitted light uniformly.

The EL spectrum of the device exhibited a vibrational structure, for which the individual peak wavelengths were the same as those in the fluorescence spectrum of the dopant (DPAVBi) from its toluene solution within a range of ±10 nm.

This device was driven in a constant current condition in a nitrogen stream at an initial luminance of 100 cd/cm$^2$, whereupon the half value period for it to have a luminance of 50 cd/cm$^2$ was 3000 hours. During the driving test, there was no change in the color of the light emitted by the device, and it was found that the device retained the ability of monomeric light emission.

These data indicate that the luminous efficiency and the life of this device are almost the same as those of the device of Example 1.

(3) Heat Resistance Test of Organic EL Device

This device was sealed and stored at 75° C. in the same manner as in Example 1. After having been thus stored for 150 hours, the color of the light emitted by the device changed, and the luminous efficiency of the device decreased to the half of the original one.

The glass transition temperature of NPD used herein was 100° C. The data obtained in this heat resistance test indicate that, even though all the organic compound layers constituting the device have a glass transition temperature of not lower than 75° C., only such is unsatisfactory for the heat resistance of the device in storage at 75° C. The difference between this device and the device of Example 1 is only in the hole transportation layer. Consideringthis, itisunderstoodthat, for the thermal stability of the organic EL device, the thermal stability of the organic compound layers adjacent to the light-emitting layer, or that is, their glass transition temperature is especially critical.

Comparative Example 2

(1) Production of Organic EL Device

An organic EL device was produced in the same manner as in Example 1, except that 4,4'-bis(2,2'-diphenylvinyl)biphenyl (DPVBI) was used as the organic host compound in place of DPVDPAN.

(2) Light Emission Test of Organic EL Device

Regarding the initial characteristics of the device at a voltage of 6 V and a current density of 1.4 mA/cm$^2$, its luminance was 102 cd/m$^2$, and its electric power conversion efficiency (luminous efficiency) was high to be 3.8 lm/W. Observing the device with the naked eye and with a luminometer (CS-100, manufactured by Minolta Co.), any non-emitting points were found on the light-emitting surface of the device and the device emitted light uniformly.

This device gave monomeric EL. The fluorescence quantum efficiency of the thin film of DPVBi was 0.4.

This device was driven in a constant current condition in a nitrogen stream at an initial luminance of 100 cd/cm$^2$, whereupon the half value period for it to have a luminance of 50 cd/cm$^2$ was 2500 hours. During the driving test, there was no change in the color of the light emitted by the device, and it was found that the device retained the ability of monomeric light emission.

These data indicate that the luminous efficiency and the life of this device are almost the same as those of the device of Example 1.

(3) Heat Resistance Test of Organic EL Device

After having been stored at 75° C. in the same manner as in Example 1, the color of the light emitted by the device changed in 20 hours, and the luminous efficiency of the device reduced greatly. The reason is because the material of the light-emitting layer, DPVBI has a low glass transition temperature of 64° C.

Comparative Example 3

(1) Production of Organic EL Device

An organic EL device was produced in the same manner as in Example 1, except that DBuPVBi was used as the organic host compound in place of DPVDPAN.

DBuPVBi was prepared by introducing tert-butyl group into the para-position of the both terminal phenyl groups of DPVBi, which was used in Comparative Example 2, in order to elevate its glass transition temperature. DBuPVBi thus had a glass transition temperature of 100° C.

(2) Light Emission Test of Organic EL Device

Regarding the initial characteristics of the device at a voltage of 6 V and a current density of 1.5 mA/cm$^2$, its luminance was 103 cd/m$^2$, and its electric power conversion efficiency (luminous efficiency) was high to be 3.6 lm/W. Observing the device with the naked eye and with a luminometer (CS-100, manufactured by Minolta Co.), any non-emitting points were found on the light-emitting surface of the device and the device emitted light uniformly.

This device gave monomeric EL. The fluorescence quantum efficiency of the thin film of DBuPVBi was 0.4.

The device was driven in a constant current condition in a nitrogen stream at an initial luminance of 100 cd/cm$^2$, whereupon its luminance decreased to the half of the original one and the color emitted by the device changed. The emission spectrum of the thus-changed device differed from the initial EL spectrum of the original device, in that the former was broad while having peaks in the longer wavelength range.

These data indicate that, even though the introduction of a bulky substituent into an organic compound is effective in elevating the glass transition temperature of the resulting compound, the life of the device comprising the compound having such a bulky substituent shall be extremely short when the device could not retain the ability of monomeric light emission. From those, it is understood that the selection of the light-emitting material to make the device have the ability of monomeric light emission is extremely critical.

Comparative Example 4

(1) Production of Organic EL Device

An organic EL device was produced in the same manner as in Example 1, except that bis(2-methyl-8-quinolato)(p-phenylphenolato) aluminium (PC7) was used as the organic host compound in place of DPVDPAN and that perylene was used as the fluorescent substance in place of DPAVBi.

(2) Light Emission Test of Organic EL Device

Regarding the initial characteristics of the device at a voltage of 6 V and a current density of 9.8 mA/cm$^2$, its luminance was 100 cd/m$^2$, and its electric power conversion efficiency (luminous efficiency) was 0.53 lm/W, or that is, it was lower than 1 lm/W. Observing the device with the naked eye and with a luminometer (CS-100, manufactured by Minolta Co.), any non-emitting points were found on the light-emitting surface of the device and the device emitted light uniformly.

The EL spectrum of the device exhibited a vibrational structure, for which the individual peak wavelengths were the same as those in the fluorescence spectrum of the dopant (perylene) from its toluene solution within a range of ±10 nm.

This device was driven in a constant current condition in a nitrogen stream at an initial luminance of 100 cd/cm$^2$, whereupon the half value period for it to have a luminance of 50 cd/cm$^2$ was 1500 hours. During the driving test, there was no change in the color of the light emitted by the device, and it was found that the device retained the ability of monomeric light emission.

However, as in the above, the luminous efficiency of this device is extremely low. The fluorescence quantum efficiency of the thin film of PC7 was 0.07. From those data obtained herein, it is understood that the high fluorescence quantum efficiency of the organic host compound used is indispensable for increasing the efficiency of the organic EL device.

TABLE 1

|  | Efficiency (lumen/W) | Ability of Monomeric Light Emission[1] | Tg (° C.) HTL[2] | Tg (° C.) Host | Life (hrs) | Stored at 75° C. (hrs) |
|---|---|---|---|---|---|---|
| Example 1 | 2.8 | ○ | 126 | 105 | 3000 | 500 or longer |
| Comparative Example 1 | 2.8 | ○ | 100 | 105 | 3000 | 150 |
| Comparative Example 2 | 3.8 | ○ | 126 | 64 | 2500 | 20 |
| Comparative Example 3 | 3.6 | X | 126 | 100 | several minutes | not measured |
| Comparative Example 4 | 0.53 | ○ | 126 | 100 | 1500 | 500 |

Notes:
[1]Ability of Monomeric Light Emission
○: The sample retained the ability of monomeric light emission.
X: The sample did not retain the ability of monomeric light emission.
[2]HTL: hole transportation layer As has been mentioned hereinabove, the organic, blue-emitting EL device of the invention has a long life and has high luminous efficiency and good thermal stability. The device is favorably used in various displays.

While the invention has been described in detail and with reference to specific embodiments thereof, it will be apparent to one skilled in the art that various changes and modifications can be made therein without departing from the spirit and scope thereof.

What is claimed is:

1. An organic electroluminescent device comprising at least one organic compound layer, of which at least one is an organic blue-emitting layer, as sandwiched between a pair of electrodes, wherein (1) the organic blue-emitting layer comprises an organic host compound having a fluorescence quantum efficiency of not smaller than 0.3 in a solid state and a fluorescent substance, and the organic host compound and the fluorescent substance are selected such that the device retains a monomeric blue-emitting ability and the fluorescent substance has an energy gap that is smaller than the energy gap of the organic host substance, and (2) all the organic compound layers have a glass transition temperature of not lower than 75° C., while the organic compound layers adjacent to the organic blue-emitting layer, when present, have a glass transition temperature of not lower than 105° C., wherein the organic host compound and the fluorescent substance are selected such that both interaction (3) between the organic host compound and the fluorescent substance and (4) between the organic host compound and any adjacent compound layer, are absent whereby said device retains said monomeric blue-emitting ability.

2. An organic electroluminescent device as claimed in claim 1, wherein the organic host compound is selected from distyrylarylene derivatives.

3. The organic electroluminescent device as claimed in claim 1, wherein at least one organic compound layer is present other than, and adjacent to, the organic blue-emitting layer and is selected from the group consisting of a hole injection layer, a hole transportation layer, and an electron injection layer.

* * * * *